(12) United States Patent
Yamada et al.

(10) Patent No.: US 11,090,617 B2
(45) Date of Patent: Aug. 17, 2021

(54) POROUS SUPPORT-ZEOLITE MEMBRANE COMPOSITE

(71) Applicant: MITSUBISHI CHEMICAL CORPORATION, Chiyoda-ku (JP)

(72) Inventors: Miki Yamada, Kanagawa (JP); Takahiko Takewaki, Kanagawa (JP); Mikio Hayashi, Kanagawa (JP); Naoko Fujita, Kanagawa (JP); Hidekazu Miyagi, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 903 days.

(21) Appl. No.: 14/467,622

(22) Filed: Aug. 25, 2014

(65) Prior Publication Data
US 2014/0360939 A1    Dec. 11, 2014

Related U.S. Application Data

(63) Continuation of application No. PCT/JP2013/054417, filed on Feb. 21, 2013.

(30) Foreign Application Priority Data

Feb. 24, 2012 (JP) .............................. JP2012-039271
Aug. 28, 2012 (JP) .............................. JP2012-187576

(51) Int. Cl.
*B01D 71/02* (2006.01)
*B01D 69/02* (2006.01)
(Continued)

(52) U.S. Cl.
CPC ......... *B01D 71/028* (2013.01); *B01D 53/228* (2013.01); *B01D 67/0051* (2013.01);
(Continued)

(58) Field of Classification Search
CPC .................................................. B01D 71/028
See application file for complete search history.

(56) References Cited

U.S. PATENT DOCUMENTS

| 5,554,286 A | 9/1996 | Okamoto et al. |
| 2002/0114958 A1 | 8/2002 | Ozeki et al. |

(Continued)

FOREIGN PATENT DOCUMENTS

| CN | 101343067 A | 1/2009 |
| CN | 102139188 A | 8/2011 |

(Continued)

OTHER PUBLICATIONS

Office Action dated Oct. 25, 2016 in Japanese Patent Application No. 2014-500936 (with unedited computer generated English translation).

(Continued)

*Primary Examiner* — Jason M Greene
*Assistant Examiner* — Eric J McCullough
(74) *Attorney, Agent, or Firm* — Oblon, McClelland, Maier & Neustadt, L.L.P.

(57) ABSTRACT

A porous support-zeolite membrane composite comprising an inorganic porous support and a zeolite membrane provided on, wherein the zeolite membrane contains a zeolite having a microporous structure of 8-membered oxygen ring or less, and a molar ratio of $SiO_2/Al_2O_3$ in the zeolite membrane surface is larger by at least 20 than a molar ratio of $SiO_2/Al_2O_3$ in the zeolite membrane itself, or a water adsorption of the porous support-zeolite membrane composite at a relative pressure of 0.8, as determined from a water vapor adsorption isotherm of the porous support-zeolite membrane composite, is at least 82% of a water adsorption of the porous support-zeolite membrane composite under the same condition as above after one-week immersion of the (Continued)

porous support-zeolite membrane composite in an aqueous 90 mass % acetic acid solution at room temperature.

16 Claims, 1 Drawing Sheet

(51) Int. Cl.
| | |
|---|---|
| B01D 67/00 | (2006.01) |
| C01B 39/02 | (2006.01) |
| C07C 29/76 | (2006.01) |
| C07C 51/47 | (2006.01) |
| C01B 39/46 | (2006.01) |
| C07C 37/82 | (2006.01) |
| C01B 39/48 | (2006.01) |
| B01D 69/12 | (2006.01) |
| C30B 7/10 | (2006.01) |
| B01D 53/22 | (2006.01) |
| B01D 61/36 | (2006.01) |

(52) U.S. Cl.
CPC ......... *B01D 67/0093* (2013.01); *B01D 69/02* (2013.01); *B01D 69/125* (2013.01); *C01B 39/026* (2013.01); *C01B 39/46* (2013.01); *C01B 39/48* (2013.01); *C07C 29/76* (2013.01); *C07C 37/82* (2013.01); *C07C 51/47* (2013.01); *C30B 7/10* (2013.01); *B01D 61/362* (2013.01); *B01D 2053/221* (2013.01); *B01D 2323/12* (2013.01); *B01D 2323/24* (2013.01); *B01D 2323/40* (2013.01); *B01D 2325/02* (2013.01); *B01D 2325/12* (2013.01)

(56) References Cited

U.S. PATENT DOCUMENTS

| | | | |
|---|---|---|---|
| 2004/0229027 A1 | 11/2004 | Mori et al. | |
| 2007/0184967 A1 | 8/2007 | Mori et al. | |
| 2009/0007780 A1 | 1/2009 | Yajima et al. | |
| 2012/0024777 A1 | 2/2012 | Sugita et al. | |

FOREIGN PATENT DOCUMENTS

| | | | | |
|---|---|---|---|---|
| CN | 102285666 A | 12/2011 | | |
| CN | 102333584 A | 1/2012 | | |
| EP | 1 210 972 A2 | 6/2002 | | |
| EP | 1 428 568 A1 | 6/2004 | | |
| EP | 2 402 071 A1 | 1/2012 | | |
| JP | 7-185275 | 7/1995 | | |
| JP | 2000-237561 | 9/2000 | | |
| JP | 2003-144871 | 5/2003 | | |
| JP | WO 2010098473 A1 * | 9/2010 | ........... | B01D 53/228 |
| JP | 2011-079818 | 4/2011 | | |
| JP | 2011-121040 | 6/2011 | | |
| JP | 2011-121045 | 6/2011 | | |
| JP | 2011-121854 | 6/2011 | | |
| JP | 2011-241097 | 12/2011 | | |
| WO | WO 0196106 A1 * | 12/2001 | ............ | B82Y 30/00 |
| WO | 2010/098473 | 9/2010 | | |

OTHER PUBLICATIONS

Combined Chinese Office Action and Search Report dated Aug. 4, 2015 in Patent Application No. 201380010119.0 (with English language translation and English language translation of categories of cited documents).
Extended European Search Report dated Mar. 5, 2015 in Patent Application No. 13751699.3.
U.S. Appl. No. 14/467,622, filed Aug. 25, 2014, Yamada, et al.
U.S. Appl. No. 14/467,496, filed Aug. 25, 2014, Hayashi, et al.
International Search Report dated May 21, 2013 in PCT/JP2013/054417 filed Feb. 21, 2013.
Combined Office Action and Search Report dated Nov. 7, 2016 in Chinese Patent Application No. 201380010119.0 (with partial unedited computer generated English language translation and English translation of categories of cited documents).
"Common knowledge—P68 of Evidence D3, i.e., Inorganic Membrane Separation Technology and Application" Mar. 31, 2003, p. 68 (with English language translation).
"Common knowledge—P387 of Evidence D4, i.e., Membrane Science and Technology" Jun. 30, 2004, pp. 385-387 (with English language translation).
"Common knowledge—P278 of Evidence D5, i.e., Preparation and Application of Separation Membrane" Feb. 29, 2004, p. 278 (with English language translation).
Office Action dated Aug. 1. 2017 in Chinese Patent Application No. 201380010119.0 (with unedited computer generated English translation).
Office Action dated Dec. 3, 2018 issued in corresponding Korean patent application 10-2014-7023103 (with English translation).
Office Action dated Jun. 29, 2018 issued in corresponding European patent application No. 13 751 699.3.

\* cited by examiner

[Fig. 1]
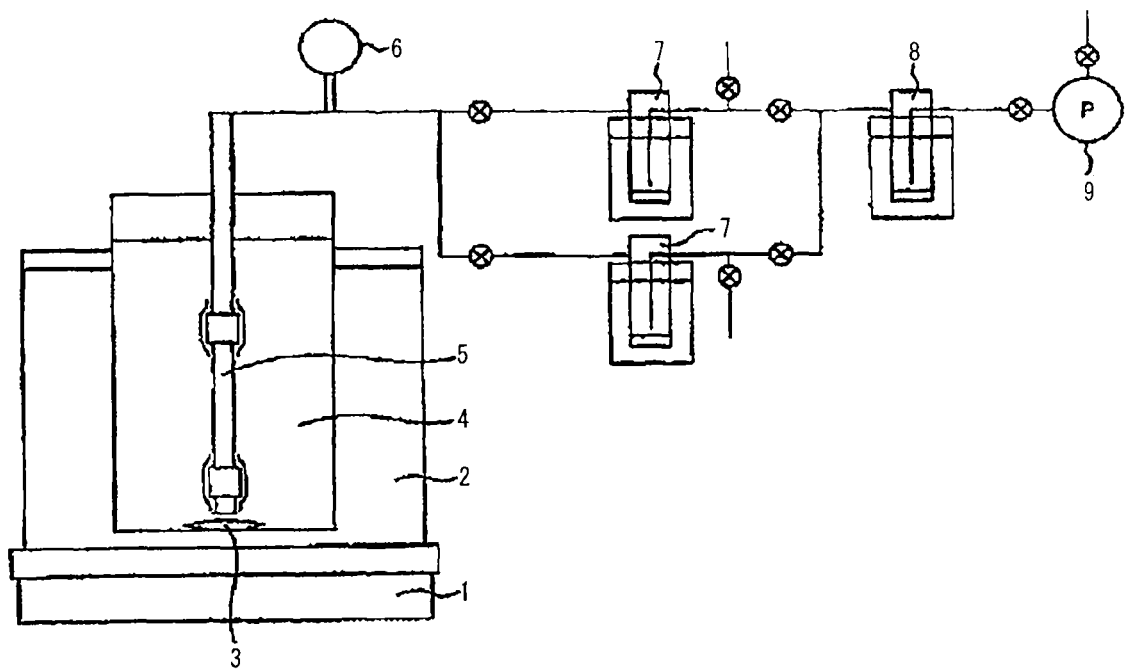
[Fig. 2]
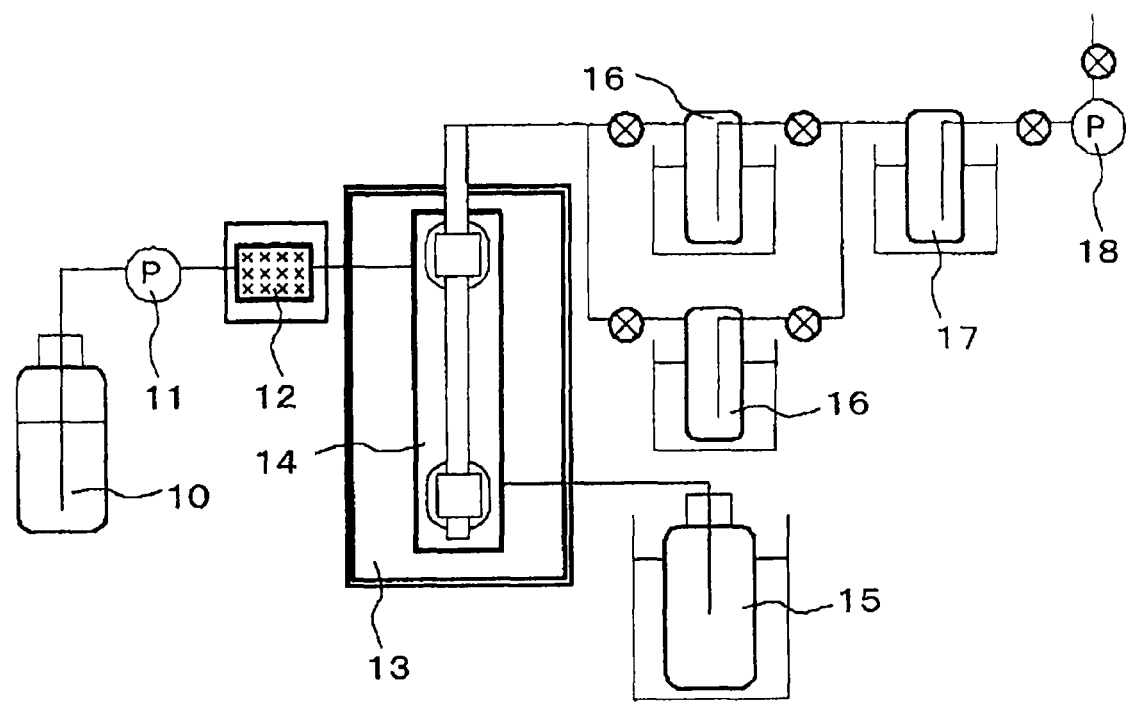

POROUS SUPPORT-ZEOLITE MEMBRANE COMPOSITE

TECHNICAL FIELD

The present invention relates to a porous support-zeolite membrane composite, and more precisely to a porous support-zeolite membrane composite that comprises a zeolite membrane having specific physiochemical properties formed on an inorganic porous support. The porous support-zeolite membrane composite of the invention can separate a highly-permeative substance through permeation from a gas or liquid mixture comprising multiple components to thereby concentrate the poorly-permeative substance in the mixture.

BACKGROUND ART

Heretofore, separation and concentration of a gas or liquid mixture that contains an organic compound is carried out through distillation, azeotropic distillation, solvent extraction/distillation, adsorption or the like, in accordance with the properties of the targeted substance. However, these methods have disadvantages in that they require much energy or the application range thereof to the subject to be separated or concentrated is limitative.

Recently, as a separation method capable of being an alternative to these methods, there has been proposed a membrane separation/concentration method using a membrane such as a polymer membrane, a zeolite membrane or the like. A polymer membrane, for example, a flat membrane, a hollow fiber membrane or the like is excellent in workability but is defective in that the heat resistance thereof is poor. In addition, as poorly resistant to chemicals, many types of polymer membranes often swell especially in contact with an organic compound such as an organic solvent or an organic acid, and therefore the application range thereof to the subject to be separated or concentrated is limitative.

A zeolite membrane is generally used for separation and concentration as a zeolite membrane composite having a filmy zeolite formed on a support. For example, a mixture of an organic compound and water is brought into contact with a zeolite membrane composite so as to make water selectively pass therethrough, to thereby separate and concentrate the organic compound. As compared with distillation or separation with an adsorbent, the separation and concentration using a membrane of an inorganic material can reduce the amount of energy to be used, and in addition, the separation and concentration with such an inorganic material membrane can be carried out in a broader temperature range than that with a polymer membrane, and further the inorganic material membrane is applicable to separation of a mixture that contains an organic compound.

As a separation method using a zeolite membrane, for example, there have been proposed a method of selective permeation of water using an A-type zeolite membrane composite for alcohol concentration (PTL 1), a method of selective permeation of water from a mixed system of alcohol and water by the use of a mordenite-type zeolite membrane composite for alcohol concentration (PTL 2), a method of selective permeation of water from a mixed system of acetic acid and water by the use of a ferrierite-type zeolite membrane composite for separation and concentration of acetic acid (PTL 3), etc.

CITATION LIST

Patent Literature

PTL 1: JP-A 7-185275
PTL 2: JP-A 2003-144871
PTL 3: JP-A 2000-237561

SUMMARY OF INVENTION

Technical Problem

However, the hitherto-proposed membrane composites, for example, the mordenite-type zeolite membrane composite in PTL 2 and the ferrierite-type zeolite membrane composite in PTL 3 could provide a small permeation flux and their throughput is insufficient for practical use. In addition, owing to promotion of dealumination under an acidic condition, the separation performance with the membrane composite may change with the prolongation of the operating time, and therefore using the membrane composite under the condition where an organic acid exists is undesirable. The A-type zeolite in PTL 1 does not have acid resistance and waterproofness, and the application range thereof is therefore limited.

Regarding many zeolite membranes, there is generally known a phenomenon that, when the concentration of the poorly-permeative substance to constitute a mixture is high, then the permeation of the poorly-permeative substance toward the permeation side may increase, and therefore the separation performance of the membrane decreases; and consequently, it is desired to realize a zeolite membrane capable of securing high separation performance even in such a case where the concentration of the poorly-permeative substance is high.

An object of the invention is to provide a porous support-zeolite membrane composite that satisfies both sufficient throughput and separation performance enough for practical use in separation and concentration through an inorganic material separation membrane, and a method of separation and concentration using the zeolite membrane composite.

Solution to Problem

The present inventors have assiduously studied for the purpose of solving the above-mentioned problems and, as a result, have found that, when a certain type of zeolite is formed as a membrane on an inorganic porous support, then there can be obtained a zeolite membrane composite capable of satisfying both sufficient throughput and separation performance enough for practical use, and have made previous proposals (WO2010/098473, JP-A 2011-121040, JP-A 2011-121045, JP-A 2011-121854). The inventors have further made additional studies and, as a result, have found that, when the properties of the surface of the zeolite membrane on the porous support are controlled to thereby make the zeolite membrane on the porous support have specific physicochemical properties, then the separation performance of the zeolite membrane can be exponentially improved. The present invention has been made on the basis of these findings.

Specifically, the gist of the invention resides in the following (1) to (15):

(1) A porous support-zeolite membrane composite comprising an inorganic porous support and a zeolite membrane provided on, wherein the zeolite membrane contains a zeolite having a microporous structure of 8-membered oxygen ring or less, and a molar ratio of $SiO_2/Al_2O_3$ in the zeolite membrane surface is larger by at least 20 than a molar ratio of $SiO_2/Al_2O_3$ in the zeolite membrane itself.

(2) The porous support-zeolite membrane composite according to the item (1) above, wherein a water adsorption of the porous support-zeolite membrane composite at a relative pressure of 0.8, as determined from a water vapor adsorption isotherm of the porous support-zeolite membrane composite, is at least 82% of a water adsorption of the porous support-zeolite membrane composite under the same condition as above after one-week immersion of the porous support-zeolite membrane composite in an aqueous 90 mass % acetic acid solution at room temperature.

(3) A porous support-zeolite membrane composite comprising an inorganic porous support and a zeolite membrane provided on, wherein the zeolite membrane contains a zeolite having a microporous structure of 8-membered oxygen ring or less, and a water adsorption of the porous support-zeolite membrane composite at a relative pressure of 0.8, as determined from a water vapor adsorption isotherm of the porous support-zeolite membrane composite, is at least 82% of a water adsorption of the porous support-zeolite membrane composite under the same condition as above after one-week immersion of the zeolite membrane composite in an aqueous 90 mass % acetic acid solution at room temperature.

(4) The porous support-zeolite membrane composite according to the item (3) above, wherein a molar ratio of $SiO_2/Al_2O_3$ in the zeolite membrane surface is larger by at least 20 than a molar ratio of $SiO_2/Al_2O_3$ in the zeolite membrane itself.

(5) The porous support-zeolite membrane composite according to any one of the item 1 to item 4 above, wherein the molar ratio of $SiO_2/Al_2O_3$ in the zeolite membrane surface is from 25 to 3000.

(6) The porous support-zeolite membrane composite according to any one of the item (1) to item (5) above, wherein the molar ratio of $SiO_2/Al_2O_3$ in the zeolite membrane itself is from 5 to 2000.

(7) The porous support-zeolite membrane composite according to any one of the item (1) to item (6) above, wherein the zeolite having a microporous structure of 8-membered oxygen ring or less is a CHA-type zeolite.

(8) The porous support-zeolite membrane composite according to any one of the item (1) to item (7) above, wherein in a X-ray diffraction pattern obtained through irradiation to the zeolite membrane surface with X-ray, a peak intensity at around $2\theta=17.9°$ is at least 0.5 times a peak intensity at around $2\theta=20.8°$.

(9) The porous support-zeolite membrane composite according to any one of the item (1) to item (8) above, wherein in a X-ray diffraction pattern obtained through irradiation to the zeolite membrane surface with X-ray, a peak intensity at around $2\theta=9.6°$ is at least 2 times a peak intensity at around $2\theta=20.8°$.

(10) The porous support-zeolite membrane composite according to any one of the item (1) to item (9) above, wherein the zeolite membrane is formed through a hydrothermal synthesis using an aqueous reaction mixture that contains an Si element source, an Al element source and an alkali source.

(11) The porous support-zeolite membrane composite according to the item (10) above, wherein the alkali source contains at least potassium.

(12) The porous support-zeolite membrane composite according to any one of the item (1) to item (11) above, wherein the zeolite membrane is, after formed through a hydrothermal synthesis, immersion-treated in a solution containing an Si element source.

(13) A separation or concentration method, which comprises bringing a gas or liquid mixture of multiple components into contact with the porous support-zeolite membrane composite as stated in any one of the item (1) to item (12) above to thereby make a highly-permeative substance in the mixture pass through the membrane composite so as to separate the highly-permeative substance from the mixture, or to thereby make the highly-permeative substance separated from the mixture so as to concentrate a poorly-permeative substance in the mixture.

(14) The method according to the item (13) above, wherein the gas or liquid mixture of multiple components is a mixture of an organic compound and water.

(15) The method according to the item (14) above, wherein the organic compound is at least one compound selected from a group consisting of organic acids, alcohols, ethers, aldehydes, ketones, esters and nitrogen-containing organic compounds.

Advantageous Effects of the Invention

According to the invention, there is provided a porous support-zeolite membrane composite capable of securing sufficiently high throughput and securing sufficient separation performance enough for practical use in separation and concentration of a specific substance from a gas or liquid mixture that comprises multiple components. Using the zeolite membrane composite as a separation means enables separation of a highly-permeative substance from a gas or liquid mixture comprising multiple components and enables concentration of the mixture.

BRIEF DESCRIPTION OF DRAWINGS

FIG. 1 is a schematic view of a measurement apparatus used in a pervaporation method.

FIG. 1 is a schematic view of a measurement apparatus used in a vapor permeation method.

DESCRIPTION OF EMBODIMENTS

Embodiments of the invention are described in more detail hereinunder. However, the description of the constituent features given below is for some examples of embodiments of the invention, and the invention is not limited by the contents thereof but can be carried out in various modifications within the spirit and the scope thereof.

The porous support-zeolite membrane composite of the invention is a porous support-zeolite membrane composite having a zeolite membrane formed on an inorganic porous support, wherein the zeolite membrane contains a zeolite having a microporous structure composed of at most 8-membered oxygen rings and wherein the molar ratio of $SiO_2/Al_2O_3$ in the zeolite membrane surface is larger by at least 20 than the molar ratio of $SiO_2/Al_2O_3$ in the zeolite membrane itself.

The porous support-zeolite membrane composite of another aspect of the invention is a porous support-zeolite membrane composite having a zeolite membrane formed on an inorganic porous support, wherein the zeolite membrane contains a zeolite having a microporous structure composed of at most 8-membered oxygen rings and wherein the water adsorption of the porous support-zeolite membrane composite at a relative pressure of 0.8, as determined from the water vapor adsorption isotherm of the porous support-zeolite membrane composite, is at least 82% of the water adsorption of the porous support-zeolite membrane composite after one-week immersion of the zeolite membrane composite in an aqueous 90 mass % acetic acid solution at room temperature.

First, the porous support-zeolite membrane composites of those aspects of the invention are described in detail hereinunder, and next, the invention relating to a separation or concentration method that uses the zeolite membrane composite as a membrane separation means. In this description, "porous support-zeolite membrane composite" may be abbreviated as "zeolite membrane composite" or as "membrane composite", and "inorganic porous support" may be abbreviated as "porous support" or as "support".

<Porous Support>

In the invention, the porous support may be any and every support of an inorganic porous material (inorganic porous support) having chemical stability in such that zeolite can be crystallized as a membrane on the surface thereof. For example, there are mentioned sintered ceramics of silica, α-alumina, γ-alumina, mullite, zirconia, titania, yttria, silicon nitride, silicon carbide or the like (ceramic supports), sintered metals of iron, bronze, stainless or the like, glass, carbon compacts, etc.

Of those porous supports, preferred are inorganic porous supports produced by sintering a solid material of a ceramic substance of which the basic component or a major part is composed of an inorganic nonmetallic substance (ceramic supports). A part of the support can form a zeolite during synthesis of the zeolite membrane thereon, and therefore using the support of the type is effective for enhancing the interlayer adhesiveness between the support and the zeolite membrane.

Concretely, for example, there are mentioned sintered ceramics of silica, α-alumina, γ-alumina, mullite, zirconia, titania, yttria, silicon nitride, silicon carbide or the like (ceramic supports). Of those, preferred is the inorganic porous support that contains at least one of alumina, silica and mullite. Using the support of the type facilitates partial zeolitation and therefore facilitates formation of a dense membrane having good separation performance owing to the firm bonding between the support and the formed zeolite.

The shape of the porous support is not specifically defined so far as the support secures efficient separation of a gas mixture or a liquid mixture. Concretely, for example, there are mentioned tabular, tubular, cylindrical, columnar or prismatic, honeycomb bodies or monolith bodies having many pores.

In the invention, zeolite is formed as a membrane on such a porous support, or that is, on the surface of the support. The surface of the support may be any one in accordance with the shape of the support, and may have multiple faces. For example, in the case of a cylindrical tubular support, zeolite may be formed on the outer surface or the inner surface thereof, and as the case may be, zeolite may be formed on both surfaces.

The mean pore size in the porous support surface is not specifically defined, in which, however, the pore size is preferably controlled. The mean pore size in the support surface is generally at least 0.02 μm, preferably at least 0.05 μm, more preferably at least 0.1 and is generally at most 20 μm, preferably at most 10 μm, more preferably at most 5 μm. When the mean pore size is not lower than the above-mentioned lower limit, then the permeation amount could increase; and when not larger than the above-mentioned upper limit, then the strength of the support itself could be sufficient and the proportion of the pores in the support surface tends to reduce to thereby facilitate the formation of a dense zeolite membrane. The measurement method for the mean pore size in the porous support surface is a mercury intrusion method.

The mean thickness (wall thickness) of the porous support is generally at least 0.1 mm, preferably at least 0.3 mm, more preferably at least 0.5 mm, and is generally at most 7 mm, preferably at most 5 mm, more preferably at most 3 mm. The support is used here for the purpose of imparting mechanical strength to the zeolite membrane, and when the mean thickness of the support is not less than the above-mentioned lower limit, then the zeolite membrane composite could have a sufficient strength and therefore the zeolite membrane composite tends to be well resistant to impact, vibration, etc. When the mean thickness of the support is not more than the upper limit, then the diffusion of the permeated substance betters and the permeation flux tends to increase.

The porosity of the porous support is generally at least 20%, preferably at least 25%, more preferably at least 30%, and is generally at most 70%, preferably at most 60%, more preferably at most 50%. The porosity of the support governs the permeation flow rate in gas or liquid separation, and when the porosity is not less than the lower limit, then the diffusion of the permeated matter would not be interfered with; and when not more than the upper limit, then the strength of the support could increase. The measurement method for the porosity of the porous support is a mercury intrusion method.

The surface of the porous support is preferably smooth, and if desired, the surface may be polished by filing or the like. The surface of the porous support means the surface part of the inorganic porous support on which zeolite is crystallized, and may be any area of the support having a different shape, and may also be multiple faces of the support. For example, in the case of a cylindrical tubular support, zeolite may be formed on any of the outer surface and the inner surface or may also be formed on both surfaces of the inner surface and the outer surface.

<Zeolite Membrane Composite>

In the invention, a zeolite membrane is formed on the above-mentioned porous support to give a zeolite membrane composite.

The components to constitute the zeolite membrane may include, in addition to zeolite, any other inorganic binder such as silica, alumina or the like, as well as an organic compound such as a polymer, and optionally a silylating agent for modifying the surface of zeolite. The zeolite membrane in the invention may partially contain an amorphous component, but is preferably a zeolite membrane substantially formed of zeolite alone.

Not specifically defined, the thickness of the zeolite membrane falls within a range of generally at least 0.1 μm, preferably at least 0.6 μm, more preferably at least 1.0 μm, and generally at most 100 μm, preferably at most 60 μm, more preferably at most 20 μm. When the membrane thickness is not more than the above-mentioned upper limit, then the permeation amount could increase; and when not less than the above-mentioned lower limit, then the selectivity may increase and the membrane strength may increase.

Not specifically defined, the grain size of zeolite is generally at least 30 nm, preferably at least 50 nm, more preferably at least 100 nm, and the upper limit thereof is not more than the thickness of the membrane. When the grain size is not less than the above-mentioned lower limit, then the grain boundary may reduce and the membrane selectivity or the like may be thereby improved. More preferred is a case where the grain size is the same as the thickness of the membrane. When the grain size of zeolite is the same as the thickness of the membrane, then the grain boundary of zeolite could be the smallest. The zeolite membrane obtained through hydrothermal synthesis to be mentioned below is especially preferred since the grain size of zeolite could be the same as the thickness of the membrane.

The shape of the zeolite membrane composite is not specifically defined, for which is employable any and every shape including tubular, hollow-fiber, monolithic, honeycomb and the like shapes. The size is not also specifically defined. For example, in the case of a tabular composite, in general, the preferred range for practical use thereof is such that the length is 2 cm or more and 200 cm or less, the inner diameter is 0.05 cm or more and 2 cm or less and the thickness is 0.5 mm or more and 4 mm or less.

One separation function of the zeolite membrane is separation as a molecular sieve, and the membrane can favorable separate gas molecules or liquid molecules having a size larger than the effective pore size of the zeolite used from gas or liquid molecules smaller than those molecules. The size of the molecules to be separated is not specifically defined, but the molecular size is generally not larger than 100 Å or so.

In the invention, the zeolite membrane is preferably such that the molar ratio of $SiO_2/Al_2O_3$ in the zeolite membrane surface (hereinafter this may be referred to as "SAR in membrane surface") is larger by at least 20 than the molar ratio of $SiO_2/Al_2O_3$ in the zeolite membrane itself (hereinafter this may be referred to as "SAR in membrane itself").

Here, in the invention, the molar ratio of $SiO_2/Al_2O_3$ in the zeolite membrane itself is a value obtained through scanning electron microscope-energy dispersive X-ray spectroscopy (SEM-EDX). In SEM-EDX, the sample is analyzed at an X-ray accelerating voltage of 10 kV or so to give the information of the membrane alone having a thickness of a few microns. Since the zeolite membrane is formed uniformly, the measurement provides SAR in the membrane itself.

The molar ratio of $SiO_2/Al_2O_3$ in the zeolite membrane surface is a value obtained through X-ray photoelectron spectroscopy (XPS). XPS is an analytical procedure of obtaining the information of the membrane surface, and according to the analytical procedure, SAR in the membrane surface can be obtained.

Zeolite is preferably an aluminosilicate, and the molar ratio of $SiO_2/Al_2O_3$ in the zeolite membrane itself is preferably at least 5, more preferably at least 8, even more preferably at least 10, still more preferably at least 12, and is preferably at most 2000, more preferably at most 1000, even more preferably at most 500, still more preferably at most 100. When SAR in the membrane itself is not less than the above-mentioned lower limit, then the durability of the membrane could better; and when not more than the upper limit, then the hydrophobicity of the membrane would not be too strong and therefore the permeation flux though the membrane could be large.

The ratio of $SiO_2/Al_2O_3$ in the zeolite membrane surface is preferably at least 25, more preferably at least 28, even more preferably at least 30, still more preferably at least 32, and is preferably at most 3000, more preferably at most 2000, even more preferably at most 1000, still more preferably at most 500. When SAR in the membrane surface is not less than the above-mentioned lower limit, then the durability of the membrane could better; and when not more than the upper limit, then the hydrophobicity of the membrane is not too strong and therefore the permeation flux though the membrane could be large.

In the invention, SAR in the membrane surface is preferably larger by at least 20 than SAR in the membrane itself, and the value (value calculated by subtracting SAR in the membrane itself from SAR in the membrane surface) is preferably at least 22, more preferably at least 25, even more preferably at least 30. The upper limit of the value is not specifically defined, but is generally at most 1000, preferably at most 700, more preferably at most 500, even more preferably at most 400.

In case where the above-mentioned value (value calculated by subtracting SAR in the membrane itself from SAR in the membrane surface) is larger than 20, then the hydrophilicity improvement of the membrane surface could be sufficient and the separation performance of the membrane therefore may better.

In the invention, the water adsorption of the porous support-zeolite membrane composite at a relative pressure of 0.8 as determined from the water vapor adsorption isotherm of the porous support-zeolite membrane composite (hereinafter this may be referred to as "water adsorption before immersion in acetic acid") is at least 82% of the water adsorption of the porous support-zeolite membrane composite under the same condition as above after one-week immersion of the porous support-zeolite membrane composite in an aqueous 90 mass % acetic acid solution at room temperature (hereinafter this may be referred to as "water adsorption after immersion in acetic acid").

Here, the adsorption isotherm is a graph showing the adsorption change relative to pressure at a constant temperature of material. In this, in general, the horizontal axis indicates the relative pressure derived by dividing the equilibrium pressure by the saturated vapor pressure ($P/P_0$), which takes a value of from 0 to 1. The index in the invention is the water (water vapor) adsorption (g/g) of the porous support-zeolite composite membrane at a relative pressure of 0.8.

Room temperature is a laboratorial temperature under no strict temperature control. In determining the influence of acetic acid immersion of the zeolite membrane composite on the water adsorption thereof, any strict temperature control of the aqueous acetic acid solution is not needed, but room temperature is generally 15° C.

In the invention, porous supports such as the above-mentioned sintered ceramics and sintered metals have an extremely small water adsorption as generally known. Concretely, the water adsorption per gram of a porous support, Nikkato's mullite tube PM at a relative pressure of 0.8 is 0.00108 g, and is less than 1/10 of the water adsorption, 0.01423 g, of the mullite tube PM-CHA zeolite membrane complex at a relative pressure of 0.8, as shown in Comparative Example 6 given hereinunder. Specifically, it may be considered that the water adsorption of the porous support-zeolite membrane composite is substantially the water adsorption of the zeolite membrane.

In the invention, the water adsorption of the porous support-zeolite membrane composite after acetic acid immersion is preferably at least 82% of the water adsorption thereof before acetic acid immersion, more preferably at least 85%, even more preferably at least 90%.

The value indicates the easiness in adsorption of acetic acid to the zeolite membrane, and the larger value means that the membrane could more hardly adsorb acetic acid. When the porous support-zeolite membrane composite of such that the water adsorption thereof after acetic acid immersion is at least 82% of the porous support-zeolite membrane composite before acetic acid immersion is used, for example for separation of acetic acid, then adsorption of acetic acid to the zeolite membrane could be inhibited therefore enabling efficient separation.

In the invention, the zeolite membrane contains a zeolite having a microstructure of 8-membered oxygen ring or less.

The main zeolite that constitutes the zeolite membrane is preferably a zeolite having a microstructure of 8-membered oxygen ring or less, more preferably a zeolite having a microstructure of from 6- to 8-membered oxygen ring.

The value n of the n-membered oxygen ring as referred to herein indicates the largest oxygen number of the pores each composed of oxygen and T elements (other elements than oxygen constituting the framework) to form the zeolite framework. For example, in a case where 12-membered oxygen rings and 8-membered oxygen rings exist together like in an MOR-type zeolite, the 12-membered oxygen rings are considered to be the n-membered oxygen rings here.

Zeolite having a microstructure of 8-membered oxygen ring or less includes, for example, AEI, AFG, ANA, BRE, CAS, CDO, CHA, DDR, DOH, EAB, EPI, ERI, ESV, FAR, FRA, GIS, GIU, GOO, ITE, KFI, LEV, LIO, LOS, LTN, MAR, MEP, MER, MEL, MON, MSO, MTF, MTN, NON, PAU, PHI, RHO, RTE, RTH, RUT, SGT, SOD, TOL, TSC, UFI, VNI, YUG, etc.

Zeolite having a microstructure of from 6- to 8-membered oxygen rings includes, for example, AEI, AFG, ANA, CHA, EAB, ERI, ESV, FAR, FRA, GIS, ITE, KFI, LEV, LIO, LOS, LTN, MAR, PAU, RHO, RTH, SOD, TOL, UFI, etc.

In this description, as described above, the zeolite structure is expressed by the code that defines the zeolite structure as stipulated by International Zeolite Association (IZA).

The n-membered oxygen ring structure defines the size of the pores of zeolite. In zeolite having micropores with at least 6-membered oxygen ring, the pore diameter is larger than the kinetic diameter of $H_2O$ molecule, and therefore the zeolite of the type secures a large permeation flux and is practicable. Of those with 8-membered oxygen ring or less, the pore diameter is small, and the zeolite of the type could have an increased separation capability for large-size organic compounds, could therefore be used for various purposes. The proportion of zeolite having a microporous structure of 8-membered oxygen ring or less in the zeolite membrane is generally at least 10% by volume, preferably at least 30% by volume, more preferably at least 60% by volume, even more preferably at least 80% by volume, most preferably 100% by volume. The proportion of zeolite having a microporous structure of from 6- to 8-membered oxygen ring in the zeolite membrane is generally at least 10% by volume, preferably at least 30% by volume, more preferably at least 60% by volume, even more preferably at least 80% by volume, most preferably 100% by volume.

Not specifically defined, the framework density (T/1000 $Å^3$) of zeolite is generally at most 17, preferably at most 16, more preferably at most 15.5, even more preferably at most 15, and is generally at least 10, preferably at least 11, more preferably at least 12.

The framework density means the number of the other elements (I elements) than oxygen to constitute the framework per 1000 $Å^3$ of zeolite, and the value is determined by the structure of zeolite. The relationship between the framework density and the zeolite structure is shown in ATLAS OF ZEOLITE FRAMEWORK TYPES Fifth Revised Edition 2001, ELSEVIER.

In the invention, preferred zeolite structures are AEI, AFG, CHA, EAB, ESV, FAR, FRA, GIS, ITE, KFI, LEV, LIO, LOS, LTN, MAR, PAU, RHO, RTH, SOD, TOL and UFI; more preferred are AEI, CHA, ERI, KFI, LEV, PAU, RHO, RTH and UFI; even more preferred are CHA and LEV; and most preferred is CHA.

Here, in the invention, the CHA-type zeolite indicates a zeolite of which the structure is expressed by a code CHA that defines a zeolite structure as stipulated by International Zeolite Association (IZA). This is a zeolite having a crystal structure equivalent to that of a natural product, chabazite. The CHA-type zeolite has a structure that has three-dimensional micropores with 8-membered oxygen rings each having a diameter of 3.8×3.8 Å, and the structure is characterized by the X-ray diffraction data thereof.

The framework density (T/1000 $Å^3$) of the CHA-type zeolite is 14.5. The molar ratio of $SiO_2/Al_2O_3$ thereof is the same as described above.

In the zeolite membrane composite of the invention where the zeolite membrane contains a CHA-type zeolite, it is desirable that, in the X-ray diffraction pattern thereof, the peak intensity at around $2θ=17.9°$ is at least 0.5 times the peak intensity at around $2θ=20.8°$.

Here, the peak intensity indicates a value obtained by subtracting the background value from the measured value. The peak intensity ratio represented by (peak intensity at around $2θ=17.9°$)/(peak intensity at around $2θ=20.8°$) (hereinafter this may be referred to as "peak intensity ratio A") is generally at least 0.5, preferably at least 1, more preferably at least 1.2, even more preferably at least 1.5. The upper limit is not specifically defined, by is generally at most 1000.

In the zeolite membrane composite where the zeolite membrane contains a CHA-type zeolite, it is desirable that, in the X-ray diffraction pattern thereof, the peak intensity at around $2θ=9.6°$ is at least 2 times the peak intensity at around $2θ=20.8°$.

The peak intensity ratio represented by (peak intensity at around $2θ=9.6°$/(peak intensity at around $2θ=20.8°$) (hereinafter this may be referred to as "peak intensity ratio B") is generally at least 2, preferably at least 2.5, more preferably at least 3, even more preferably at least 4, further more preferably at least 6, still more preferably at least 8, and most preferably at least 10. The upper limit is not specifically defined, by is generally at most 1000.

Here, the X-ray diffraction pattern is drawn through irradiation of the surface to which zeolite mainly adheres, with X-rays from a ray source of CuKα followed by scanning with a scan axis of θ/2θ. The shape of the sample to be analyzed may be any one of which the surface of the membrane composite having zeolite mainly adhering thereto could be irradiated with X-rays, and as one example thereof capable of well expressing the characteristic feature of the membrane composite, preferred is the membrane composite itself just after its production or one prepared by cutting the produced membrane composite into a suitable size that is restricted by apparatus.

Here, in case where the surface of the zeolite membrane composite is a curved one, the membrane composite of the type may be analyzed to give the X-ray diffraction pattern thereof, while using an automatic variable slit and while fixing the irradiation width. The X-ray diffraction pattern in the case of using an automatic variable slit indicates a pattern with variable to stationary slit correction.

Here, the peak at around $2θ=17.9°$ indicates the maximum peak of those existing in the range of $17.9°±0.6°$ among the peaks not assigned to the substrate.

The peak at around $2θ=20.8°$ indicates the maximum peak of those existing in the range of $20.8°±0.6°$ among the peaks not assigned to the substrate.

The peak at around 2θ=9.6° indicates the maximum peak of those existing in the range of 9.6°±0.6° among the peaks not assigned to the substrate.

According to COLLECTION OF SIMULATED XRD POWDER PATTERNS FOR ZEOLITE, Third Revised Edition, ELSEVIER (1996) (hereinafter this may be referred to as "Non-Patent Literature, NPL 1") and assuming that the space group using rhombohedral setting is:

$$R\bar{3}m \quad [\text{Math. 1}]$$

(No. 166), the peak at around 2θ=9.6° in the X-ray diffraction pattern is a peak assigned to the plane with an index of (1,0,0) in the CHA structure.

Also, according to NPL 1 and assuming that the space group using rhombohedral setting is:

$$R\bar{3}m \quad [\text{Math. 2}]$$

(No. 166), the peak at around 2θ=17.9° in the X-ray diffraction pattern is a peak assigned to the plane with an index of (1,1,1) in the CHA structure.

According to NPL 1 and assuming that the space group using rhombohedral setting is:

$$R\bar{3}m \quad [\text{Math. 3}]$$

(No. 166), the peak at around 2θ=20.8° in the X-ray diffraction pattern is a peak assigned to the plane with an index of (2,0,−1) in the CHA structure.

According to Halil Kalipcilar, et al., "Synthesis and Separation Performance of SSZ-13 Zeolite Membranes on Tubular Supports", Chem. Mater, 2002, 14, 3458-3464 (hereinafter this may be referred to as "NPL 2"), the typical ratio of the (1,0,0) plane-derived peak intensity to the (2,0,−1) plane-derived peak intensity in the CHA-type aluminosilicate zeolite membrane (peak intensity ratio B) is less than 2.

Consequently, it is considered that the ratio of at least 2 could mean that the zeolite crystals have grown while aligned in such a manner that the (1,0,0) plane of the CHA structure to be, for example, rhombohedral setting could be nearly parallel to the surface of the membrane composite. In the zeolite membrane composite, growing the zeolite crystal while aligned is advantageous in that a dense membrane having high separation performance can be formed.

According to NPL 2, the typical peak of the (1,1,1) plane-derived peak intensity to the (2,0,−1) plane-derived peak intensity in the CHA-type aluminosilicate zeolite membrane (peak intensity ratio A) is less than 0.5.

Consequently, it is considered that the ratio of at least 0.5 could mean that the zeolite crystals have grown while aligned in such a manner that the (1,1,1) plane of the CHA structure to be, for example, rhombohedral setting could be nearly parallel to the surface of the membrane composite. In the zeolite membrane composite, growing the zeolite crystals while aligned is advantageous in that a dense membrane having high separation performance can be formed.

As in the above, the case where any of the peak intensity ratio A or B is a value falling within the above-mentioned specific range means that the zeolite crystals have grown while aligned to provide a dense membrane having high separation performance.

A larger value of the peak intensity ratio A or B indicates a high degree of alignment, and in general, a high degree of alignment indicates formation of a denser membrane. In general, a higher degree of alignment could provide higher separation performance, but depending on the type of the mixture to be separated, the best degree of alignment to provide high separation performance may vary; and consequently, it is desirable to select and use a zeolite membrane composite having a best degree of alignment in accordance with the type of the mixture to be separated.

<Production Method for Zeolite Membrane Composite>

In the invention, the production method for the porous support-zeolite membrane composite is not specifically defined, for which, for example, preferred is a method of forming a zeolite membrane on an inorganic porous support through hydrothermal synthesis to prepare a zeolite membrane composite, followed by immersion it in a solution containing an Si compound.

Concretely, for example, the zeolite membrane composite may be prepared by putting a reaction mixture for hydrothermal synthesis of which the composition has been prepared and homogenized (hereinafter this may be referred to as "aqueous reaction mixture") into a heat-resistant and pressure-resistant container such as an autoclave or the like in which a porous support has been gently fixed therein, airtightly sealing up the container and heating it for a predetermined period of time.

As the aqueous reaction mixture, preferred is one containing an Si element source, an Al element source, an alkali source and water, and optionally containing an organic template.

The Si element source to be used for the aqueous reaction mixture includes, for example, amorphous silica, colloidal silica, silica gel, sodium silicate, amorphous aluminosilicate gel, tetraethoxysilane (TEOS), trimethylethoxysilane, etc.

The Al element source includes, for example, sodium aluminate, aluminium hydroxide, aluminium sulfate, aluminium nitrate, aluminium oxide, amorphous aluminosilicate gel, etc. The mixture may additionally contain any other element source than the Al element source, for example, an element source of Ga, Fe, B, Ti, Zr, Sn, Zn or the like.

In crystallization of zeolite, if desired, an organic template (structure directing agent) may be used, and preferred here is one synthesized by the use of an organic template. Synthesizing by the use of an organic template increases the ratio of the silicon atom relative to the aluminium atom in the crystallized zeolite and therefore enhances the acid resistance of the zeolite.

Not specifically defined in point of the type thereof, the organic template may be any one capable of forming a desired zeolite membrane. One alone or two or more different types of templates may be used here either singly or as combined.

In case where the zeolite is a CHA-type one, in general, amines or quaternary ammonium salts are usable as the organic template. For example, preferred are the organic templates described in U.S. Pat. No. 4,544,538 and US Patent Application Publication 2008/0075656.

Concretely, for example, there are mentioned cations derived from alicyclic amines, such as cations derived from 1-adamantanamine, cations derived from 3-quinacridinal, cations derived from 3-exo-aminonorbornene, etc. Of those, more preferred are cations derived from 1-adamantanamine. When a cation derived from 1-adamantanamine is used as the organic template here, a CHA-type zeolite capable of forming a dense membrane may crystallize. In addition, a CHA-type zeolite having a sufficient hydrophilicity enough for selective water permeability of the membrane thereof may also be formed, and further a CHA-type zeolite excellent in acid resistance may be formed.

Of the cations derived from 1-adamantanamine, more preferred is an N,N,N-trialkyl-1-adamantanammonium cation. In general, the three alkyl groups of the N,N,N-trialkyl-1-adamantanammonium cation are alkyl groups independent of each other, and are preferably lower alkyl groups, more preferably methyl groups. Of the above, the most preferred compound is N,N,N-trimethyl-1-adamantanammonium cation.

The cation of the type is accompanied by an anion not causing any harm to the formation of CHA-type zeolite. Typical examples of the anion of the type include halide ions such as $Cl^-$, $Br^-$, $I^-$, etc.; as well as hydroxide ion, acetate, sulfate, and carboxylate. Of those, especially preferred for use here is a hydroxide ion.

As other organic templates, also usable are N,N,N-trialkylbenzylammonium cations. Also in the case, the alkyl groups are independent of each other, and are preferably lower alkyl groups, more preferably methyl groups. Of the above, the most preferred compound is N,N,N-trimethylbenzylammonium cation. The anion accompanied by the cation is the same as above.

The alkali source for use for the aqueous reaction mixture includes hydroxide ions of counter anions of organic templates, alkali metal hydroxides such as NaOH, KOH, etc.; alkaline earth metal hydroxides such as $Ca(OH)_2$, etc. The type of the alkali is not specifically defined, for which generally used are Na, K, Li, Rb, Cs, Ca, Mg, Sr, Ba, etc. Of those, preferred are Na and K, and more preferred is K. Two or more different types of alkalis may be used here, and concretely, combined use of Na and K is preferred.

The ratio of the Si element source and the Al element source in the aqueous reaction mixture is generally expressed as the molar ratio of oxides of the respective elements, or that is, as the molar ratio of $SiO_2/Al_2O_3$. Not specifically defined, the molar ratio of $SiO_2/Al_2O_3$ is generally at least 5, preferably at least 8, more preferably at least 10, even more preferably at least 15. Generally, the ratio is at most 10000, preferably at most 1000, more preferably at most 300, even more preferably at most 100.

The molar ratio of $SiO_2/Al_2O_3$ falling within the above range provides formation of a dense zeolite membrane and further, the formed zeolite exhibits strong hydrophilicity and, for example, enables selective penetration of a hydrophilic compound from an organic compound-containing mixture, especially water therethrough. In addition, a zeolite membrane having strong acid resistance and having dealumination resistance may be obtained. In particular, when the molar ratio of $SiO_2/Al_2O_3$ falls within the range, a CHA-type zeolite crystal of forming a dense membrane can be formed through crystallization. In addition, a CHA-type zeolite having sufficient hydrophilicity enough for selective water penetration through the membrane thereof can be formed, and a CHA-type zeolite excellent in acid resistance can be obtained.

The ratio of the silica source and the organic template in the aqueous reaction mixture is, as the ratio by mol of organic template to $SiO_2$ (molar ratio of organic template/$SiO_2$), generally at least 0.005, preferably at least 0.01, more preferably at least 0.02, and is generally at most 1, preferably at most 0.4, more preferably at most 0.2.

The molar ratio of organic template/$SiO_2$ falling within the above range provides formation of a dense zeolite membrane and, in addition thereto, the formed zeolite has strong acid resistance and Al is hardly released therefrom. Further, under the condition, an especially dense and acid-resistant CHA-type zeolite can be formed.

The ratio of Si element source and the alkali source is, as the ratio by mol of $M_{(2/n)}O/SiO_2$ (wherein M means an alkali metal or an alkaline earth metal, and n indicates the valence thereof, 1 or 2), generally at least 0.02, preferably at least 0.04, more preferably at least 0.05, and is generally at most 0.5, preferably at most 0.4, more preferably at most 0.3.

In forming a CHA-type zeolite membrane, it is desirable that the alkali metal to be used contains K, since a denser and higher crystalline membrane may be formed. In the case, the molar ratio of K to the total of all alkali metals including K and alkaline earth metals is generally from 0.01 to 1, preferably from 0.1 to 1, more preferably from 0.3 to 1.

Addition of K to the aqueous reaction mixture tends to enlarge the ratio of the peak intensity of the peak at around $2\theta=9.6°$ assigned to the plane with an index of (1,0,0) in the CHA structure, to the peak intensity of the peak at around $2\theta=20.8°$ assigned to the plane (2,0,-1) (peak intensity ratio B), or the ratio of the peak intensity of the peak at around $2\theta=17.9°$ assigned to the plane (1,1,1) to the peak intensity of the peak at around $2\theta=20.8°$ assigned to the plane (2,0,-1) (peak intensity ratio A), assuming that the space group using rhombohedral setting is:

$$R\bar{3}m \qquad \text{[Math. 4]}$$

(No. 166), as described above.

The ratio of the Si element source and water is, as the ratio by mol of water to $SiO_2$ (molar ratio of $H_2O/SiO_2$), generally at least 10, preferably at least 30, more preferably at least 40, even more preferably at least 50, and is generally at most 1000, preferably at most 500, more preferably at most 200, even more preferably at most 150.

When the molar ratios of the substances in the aqueous reaction mixture each fall within the above range, a dense zeolite membrane can be formed. The amount of water is especially important in formation of the dense zeolite membrane, and under the condition where the amount of water is larger than that of silica as compared with the ordinary condition in powdery synthesis, a dense membrane can be formed readily.

In general, the amount of water in synthesis of a powdery CHA-type zeolite is, as the molar ratio of $H_2O/SiO_2$, from 15 to 50 or so. When the molar ratio of $H_2O/SiO_2$ is increased (to be 50 or more and 1000 or less), or that is, under the condition where the amount of water is large, a zeolite membrane composite having a CHA-type zeolite crystallized on a support as a dense membrane thereon and therefore having high separation performance can be obtained.

Further, in hydrothermal synthesis, it is not always necessary to make a seed crystal present inside the reaction system, but by adding a seed crystal to the system, zeolite crystallization on a support can be promoted. The method of adding a seed crystal is not specifically defined. Like in powdery zeolite synthesis, employable here is a method of adding a seed crystal to the aqueous reaction mixture, or a method of attaching a seed crystal onto a support.

In producing the zeolite membrane composite, it is desirable that a seed crystal is attached onto a support. Previously attaching a seed crystal onto a support facilitates formation of a dense zeolite membrane having good separation performance.

Not specifically defined in point of the type thereof, the seed crystal to be used here may be any zeolite capable of promoting crystallization. Preferably, however, the same crystal type as that of the zeolite membrane to be formed is used for efficient crystallization. In case where a CHA-type zeolite membrane is formed, preferred is use of a seed crystal of CHA-type zeolite.

The grain size of the seed crystal is generally at least 0.5 nm, preferably at least 1 nm, more preferably at least 2 nm, and is generally at most 20 μm, preferably at most 15 μm, more preferably at most 10 μm.

The method of attaching a seed crystal onto a support is not specifically defined. For example, employable here are a dipping method that comprises dispersing a seed crystal in a solvent such as water or the like and then dipping a support in the dispersion to make the seed crystal adhere to the support, and a coating method that comprises mixing a seed crystal with a solvent such as water or the like to give a slurry and then applying the resulting slurry with rubbing onto a support. Preferred is the dipping method for reproducible production of a membrane composite under control of the seed crystal adhering amount.

The solvent in which the seed crystal is dispersed is not specifically defined, but water is especially preferred.

The amount of the seed crystal to be dispersed is not also specifically defined. In general, the amount is at least 0.01% by mass relative to the total mass of the dispersion, preferably at least 0.1% by mass, more preferably at most 0.3% by mass, and is generally at most 20% by mass, preferably at most 10% by mass, more preferably at most 5% by mass, even more preferably at most 4% by mass, still more preferably at most 3% by mass.

When the amount of the seed crystal to be dispersed is not less than the above-mentioned lower limit, then the amount of the seed crystal that adheres to the support could be sufficient, and therefore the support would not have any partial site where zeolite does not form during hydrothermal synthesis, and there is a high probability that a membrane with no defect can be formed. The amount of the seed crystal to adhere onto the support according to the dipping method would reach nearly a constant level when the amount of the seed crystal in the dispersion is not less than a certain level, and therefore, when the amount of the seed crystal in the dispersion is not more than the above-mentioned upper limit, then the seed crystal would go to waste little and it is advantageous in point of the production cost.

It is desirable to attach a seed crystal onto a support according to the dipping method or through slurry application and then to dry it to form a zeolite membrane.

The amount of the seed crystal to be previously attached to the support is not specifically defined. In terms of mass per m$^2$ of support, the amount is generally at least 0.01 g, preferably at least 0.05 g, more preferably at least 0.1 g, and is generally at most 100 g, preferably at most 50 g, more preferably at most 10 g, even more preferably at most 8 g.

When the amount of the seed crystal is not less than the above-mentioned lower limit, then the crystal would be easy to form, the membrane growth could be sufficient, and the membrane growth could be uniform. On the other hand, when the amount of the seed crystal is not more than the upper limit, then the surface roughness could hardly be augmented by the seed crystal, any spontaneous nuclei resulting from the seed crystal having dropped from the support could hardly grow further and therefore the membrane growth on the support would not be thereby interfered with. In any case, the above range could facilitate formation of a dense zeolite membrane.

In case where a zeolite membrane is formed on a support through hydrothermal synthesis, the method of fixing the support is not specifically defined. Herein employable is any configuration of vertical setting or horizontal setting. In this case, the zeolite membrane may be formed according to a stationary method, or may be formed while the aqueous reaction mixture is stirred.

Not specifically defined, the temperature in zeolite membrane formation is generally 100° C. or higher, preferably 120° C. or higher, more preferably 150° C. or higher, and is generally 200° C. or lower, preferably 190° C. or lower, more preferably 180° C. or lower. When the reaction temperature is not lower than the above-mentioned lower limit, zeolite could be easy to crystallize. When the reaction temperature is not higher than the upper limit, then zeolite of a type different from the type of zeolite in the invention would be difficult to form.

The heating time is not specifically defined, but is generally at least 1 hour, preferably at least 5 hours, more preferably at least 10 hours, and is generally at most 10 days, preferably at most 5 days, more preferably at most 3 days, and even more preferably at most 2 days. When the reaction time is not shorter than the above-mentioned lower limit, then zeolite would be easy to crystallize. When the reaction time is not longer than the upper limit, then zeolite of a type different from the type of zeolite in the invention would be difficult to form.

The pressure in zeolite membrane formation is not specifically defined. The autogenous pressure to arise in heating the aqueous reaction mixture put in a closed container, within the temperature range would be enough. If desired, an inert gas such as nitrogen or the like may be added to the container.

The zeolite membrane composite formed through hydrothermal synthesis is washed with water, then heat-treated and dried. Here, the heat treatment means that the zeolite membrane composite is dried by heating it, or the template, if used, is calcined.

For drying, the temperature in heat treatment is generally 50° C. or higher, preferably 80° C. or higher, more preferably 100° C. or higher, and is generally 200° C. or lower, preferably 150° C. or lower. For the template calcination, the temperature is generally 350° C. or higher, preferably 400° C. or higher, more preferably 430° C. or higher, even more preferably 480° C. or higher, and is generally 900° C. or lower, preferably 850° C. or lower, more preferably 800° C. or lower, even more preferably 750° C. or lower.

In the case of the template calcination, when the heat treatment temperature is not lower than the above-mentioned lower limit, then the proportion of the remaining organic template could be small and therefore the number of the micropores in the zeolite could increase, and as a result, the permeation flux in separation and concentration through the membrane could thereby increase. When the heat treatment temperature is not higher than the upper limit, then the difference in the coefficient of thermal expansion between the support and the zeolite could reduce and therefore the zeolite membrane would hardly crack and the zeolite membrane could thereby secure good denseness and high separation performance.

The heating time is not specifically defined so far as the zeolite membrane could be fully dried or the template could be calcined within the time, but is preferably at least 0.5 hours, more preferably at least 1 hour. The upper limit is not specifically defined but is generally at most 200 hours, preferably at most 150 hours, more preferably at most 100 hours. The heat treatment for the template calcination may be carried out in an air atmosphere, but may be carried out in an inert atmosphere such as $N_2$ or the like or in an atmosphere with oxygen added thereto.

In case where the hydrothermal synthesis is carried out in the presence of an organic template, it is suitable that, after the obtained zeolite membrane composite is washed with water, the organic template is removed, for example, through heat treatment, extraction or the like, preferably through heat treatment, or that is, calcination.

The heating speed in heat treatment for calcining the template is preferably as slow as possible in order that the difference in the coefficient of thermal expansion between the support and zeolite could provide few cracks in the zeolite membrane. The heating speed is generally at most 5° C./min, preferably at most 2° C./min, more preferably at most 1° C./min, even more preferably at most 0.5° C./min. In general, the heating speed is at least 0.1° C./min in consideration of operability.

After the calcination, the cooling speed must also be controlled so as to prevent the zeolite membrane from being cracked. Like the heating speed, the cooling speed is also preferably lower. The cooling speed is generally at most 5° C./min, preferably at most 2° C./min, more preferably at most 1° C./min, even more preferably at most 0.5° C./min. In general, the cooling speed is at least 0.1° C./min in consideration of operability.

If desired, the zeolite membrane may be ion-exchanged. The ion exchange is generally carried out after template removal in case where a template is used in synthesis. The ion to be exchanged includes proton, alkali metal ions such as $Na^+$, $K^+$, $Li^+$, etc.; Group 2 element ions such as $Ca^{2+}$, $Mg^{2+}$, $Sr^{2+}$, $Ba^{2+}$, etc.; ions of transition metals such as Fe, Cu, Zn, etc. Of those, preferred are proton, and alkali metal ions such as $Na^+$, $K^+$, $Li^+$, etc.

The ion exchange may be carried out according to a method where the zeolite membrane is, after calcined (when a template is used), treated with an aqueous solution containing an ammonium salt or an exchanging ion such as $NH_4NO_3$, $NaNO_3$ or the like, or as the case may be, with an acid such as hydrochloric acid or the like, generally at a temperature of from room temperature to 100° C., and then washed with water. Further, if desired, the membrane may be calcined at 200° C. to 500° C.

The air permeation flux [$L/(m^2 \cdot h)$] through the thus-obtained porous support-zeolite membrane composite (heat-treated zeolite membrane composite) is generally at most 1400 $L/(m^2 \cdot h)$, preferably at most 1000 $L/(m^2 \cdot h)$, more preferably at most 700 $L/(m^2 \cdot h)$, even more preferably at most 600 $L/(m^2 \cdot h)$, still more preferably at most 500 $L/(m^2 \cdot h)$, further more preferably at most 300 $L/(m^2 \cdot h)$, and most preferably at most 200 $L/(m^2 \cdot h)$. The lower limit of the permeation is not specifically defined but is generally at least 0.01 $L/(m^2 \cdot h)$, preferably at least 0.1 $L/(m^2 \cdot h)$, more preferably at least 1 $L/(m^2 \cdot h)$.

Here, the air permeation flux is the permeation flux of air [$L/(m^2 \cdot h)$] through the zeolite membrane composite as connected to a vacuum line under an absolute pressure of 5 kPa, as described below.

Subsequently, the zeolite membrane composite is immersed in a liquid at least containing an Si element source, for example, an Si compound (hereinafter this may be referred to as "silylation treatment"). Accordingly, the zeolite membrane surface is modified with the Si compound to thereby get the above-mentioned specific physicochemical properties. For example, forming a layer that contains many Si—OH's on the surface of the zeolite membrane could enhance the hydrophilicity of the membrane surface and therefore could improve the separation performance of the membrane. In addition, modifying the zeolite membrane surface with the Si compound can secondarily provide an effect of blocking the fine defects existing in the membrane surface.

Not specifically defined, the liquid to be used for the silylation treatment may be any one in which the zeolite membrane composite could be immersed under the condition of silylation treatment, and which may be a solution of an Si element source, for example, an Si compound with a solvent added thereto, or may be a liquid thereof with no solvent added thereto, and may also be a sol or a gel. Here, the solvent may be water or an organic solvent. Any one that is liquid under pressure at a temperature not lower than the boiling point thereof is also within the scope of the solvent. In this case, the pressure may be autogenous pressure or applied pressure. Further, the liquid for the silylation treatment may be any one containing at least an Si compound, and may additionally contain any other element source (compound), for example, an Al compound.

First described is the case where water is used as the solvent.

In the case where water is used as the solvent, the temperature of the solution is generally not lower than 20° C., preferably not lower than 60° C., more preferably not lower than 80° C., and is generally not higher than 200° C., preferably not higher than 150° C., more preferably not higher than 130° C. When the temperature is not lower than the above-mentioned lower limit, then the dehydrating condensation and the hydrolysis reaction to be carried out between the Si compound and the membrane surface and between the Si compounds would be sufficient so that the membrane surface could be thereby sufficiently modified by the Si compound and the hydrophilicity thereof could be fully enhanced. When the temperature is not higher than the upper limit, then there is little possibility that zeolite would partially dissolve out in water and the zeolite membrane would be thereby broken.

The immersion time is generally at least 1 hour, preferably at least 4 hours, more preferably at least 8 hours, and is generally at most 100 hours, preferably at most 50 hours, more preferably at most 24 hours. When the immersion time is not shorter than the above-mentioned lower limit, then the membrane surface could be sufficiently modified and could therefore sufficiently enjoy the effect. When the immersion time is not longer than the upper limit, then there is little possibility that zeolite would partially dissolve out in water and the zeolite membrane would be thereby broken.

Not specifically defined, the pressure during silylation treatment may be atmospheric pressure, or autogenous pressure to arise in heating the treatment solution put in a closed container within the above-mentioned temperature range would be enough. If desired, an inert gas such as nitrogen or the like may be added to the container.

As the Si compound, usable here are, for example, alkoxysilanes such as tetraethoxysilane, tetramethoxysilane, methyltriethoxysilane, 3-aminopropyltriethoxysilane, etc.; as well as amorphous silica, fumed silica, colloidal silica, silica gel, sodium silicate, silicate oligomer, silica sol, etc. Of those, preferred are alkoxysilanes from the viewpoint of reactivity; and more preferred are tetraethoxysilane and 3-aminopropyltriethoxysilane in which the content of an alkyl group is small and which could realize high hydrophilicity after hydrolysis.

As the Al compound, for example, usable here are sodium aluminate, aluminium hydroxide, aluminium sulfate, aluminium nitrate, aluminium oxide, alumina sol, amorphous aluminosilicate gel, and aluminium alkoxides such as aluminium isopropoxide, etc. Of those, preferred are aluminium alkoxides.

One alone or two or more different types of those Si compounds and Al compounds may be used here either singly or as combined.

The content of the Si compound and the Al compound in the solution is, as a total concentration of the Si element and the Al element, generally at least 0.01% by mass, preferably 0.03% by mass, more preferably 0.1% by mass, and is generally at most 20% by mass, preferably at most 10% by mass, more preferably at most 5% by mass. The concentration of the Si element is generally at least 0.01% by mass, preferably at least 0.05% by mass, more preferably at least 0.1% by mass, and is generally at most 10% by mass, preferably at most 5% by mass, more preferably at most 2% by mass.

Preferably, the solution contains an acid or a base as a catalyst for the dehydrating condensation between the zeolite surface OH group and the Si compound and between the Si compounds, and for the hydrolysis of the alkoxy group. Accordingly, the pH of the solution is generally from 0 to 12, preferably from 0.5 to 10, more preferably from 1 to 8 or so.

A slight amount of $OH^{-1}$ ions may be made to positively exist in water by adding a basic substance such as NaOH, KOH, amine or the like thereto. In the case, the $OH^{-1}$ ion concentration in the aqueous solution is generally at most 0.01 mol/l, more preferably at most 0.005 mol/l, and is generally at least 0.0001 mol/l, preferably at least 0.0005 mol/l, more preferably at least 0.001 mol/l. Presence of $OH^{-1}$ ion in water makes it possible to provide the same effect within a shorter period of time than absence thereof. When the $OH^{-1}$ ion concentration in water is not higher than the above-mentioned upper limit, the zeolite membrane would be hardly dissolved and broken and therefore any strict control of the processing time would be unnecessary.

As the acid to be added to the aqueous solution, for example, there may be mentioned organic acids such as carboxylic acids, sulfonic acids, etc., and inorganic acids such as sulfuric acid, phosphoric acid, etc. Of those, especially preferred are carboxylic acids and inorganic acids.

As the carboxylic acids, preferred are, for example, formic acid, acetic acid, propionic acid, oxalic acid, malonic acid, maleic acid, phthalic acid, lactic acid, citric acid, acrylic acid, etc.; more preferred are formic acid, acetic acid, and lactic acid; and even more preferred is acetic acid. As the inorganic acids, preferred are, for example, sulfuric acid, nitric acid, phosphoric acid, hydrochloric acid, etc.; and more preferred are sulfuric acid, nitric acid, phosphoric acid.

The concentration of the acidic substance in the aqueous solution is preferably at least 0.01 mol/l, more preferably at least 0.05 mol/l, and is preferably at most 10 mol/l, more preferably at most 1 mol/l.

The $H^+$ concentration is generally at least $1\times10^{-10}$ mol/l, preferably at least $1\times10^{-8}$ mol/l, more preferably at least $1\times10^{-7}$ mol/l, even more preferably at least $1\times10^{-5}$ mol/l, and is generally at most 10 mol/l, preferably at most 5 mol/l, more preferably at most 1 mol/l.

A basic substance may be made to be present in the aqueous solution so that the $H^+$ concentration therein could fall within the above range. The basic substance includes, for example, NaOH, KOH, amine, etc.

Next described is the immersion treatment using an organic solvent.

In this case, the temperature of the solution is generally not lower than 20° C., preferably not lower than 60° C., more preferably not lower than 80° C., and is generally not higher than 200° C., preferably not higher than 150° C., more preferably not higher than 110° C. When the temperature is not lower than the above-mentioned lower limit, then the dehydrating condensation and the hydrolysis reaction to be carried out between the Si compound and the membrane surface and between the Si compounds would be sufficient so that the membrane surface could be thereby sufficiently modified by the Si compound and the hydrophilicity thereof could be fully enhanced. When the temperature is not higher than the upper limit, then there is little possibility that zeolite would partially dissolve out in water and the zeolite membrane would be thereby broken.

The immersion time is generally at least 0.5 hours, preferably at least 1 hour, more preferably at least 3 hours, and is generally at most 50 hours, preferably at most 24 hours, more preferably at most 10 hours. When the immersion time is not shorter than the above-mentioned lower limit, then the membrane surface could be sufficiently modified and could therefore sufficiently enjoy the effect. When the immersion time is not longer than the upper limit, then there is little possibility that zeolite would partially dissolve out in water and the zeolite would be thereby broken.

The pressure during silylation treatment is not specifically defined. The silylation may be carried out under atmospheric pressure and optionally under reflux. If desired, the silylation may be carried out under autogenous pressure that would arise in heating the treatment solution put in a closed container within the above-mentioned temperature range. Further if desired, an inert gas such as nitrogen or the like may be added to the container.

The solvent to be used is, for example a nonpolar solvent such as toluene, hexane, etc.; anisole; an alcohol solvent such as isopropyl alcohol, etc.; and polar solvent such as acetone, etc. Of those, especially preferred are toluene, isopropyl alcohol. One alone or two or more different types of those solvents may be used here either singly or as combined.

Further, in case where an organic solvent is used, water may be added into the system. The concentration of water to be added is generally at least 0.001% by mass, preferably at least 0.05% by mass, more preferably at least 0.2% by mass, and is generally at most 5% by mass, preferably at most 3% by mass, more preferably at most 2% by mass.

The type of the Si compound and the type of the Al compound to be used are the same as those in the case where water is used as the solvent. As the Si compound in this case, preferred are alkoxysilanes, and more preferred are tetraethoxysilane and 3-aminopropyltriethoxysilane. As the Al compound, especially preferred are aluminium alkoxides.

One alone or two or more different types of those Si compounds and Al compounds may be used here either singly or as combined.

The content of the Si compound is, as the Si element concentration, generally at least 0.01% by mass, preferably at least 0.05% by mass, more preferably at least 0.1% by mass, and is generally at most 10% by mass, preferably at most 5% by mass, more preferably at most 2% by mass. The content of the Al compound is, as the Al element concentration, generally at least 0.01% by mass, preferably at least 0.05% by mass, more preferably at least 0.1% by mass, and is generally at most 10% by mass, preferably at most 5% by mass, more preferably at most 1% by mass.

In the silylation treatment, the system may be treated without addition of any solvent thereto before immersed in a liquid containing at least an Si element source, for example, an Si compound. In particular, in case where a silicate oligomer is used as the Si compound, any solvent may not be added to the system. Even in the case where a solvent is not further added, the system may contain any other element source (compound), for example, an Al compound.

The immersion temperature in the case of silylation without addition of any solvent is generally 1° C. or higher, preferably 5° C. or higher, more preferably 10° C. or higher, even more preferably 15° C. or higher, and is generally 200° C. or lower, preferably 150° C. or lower, more preferably 130° C. or lower, even more preferably 100° C. or lower, most preferably 80° C. or lower. When the temperature is not lower than the lower limit, the flowability of the Si compound could be higher so that the Si compound and the Al compound could attach uniformly to the surface of the zeolite membrane composite without any trouble of partial modification of the surface. When the temperature is not higher than the upper limit, then the reaction between the Si compounds or Al compounds and the reaction between the Si compound and the Al compound could go on slowly, and the compounds could fully attach to the zeolite membrane composite surface could fully react thereon.

The immersion time is generally at least 0.5 seconds, preferably at least 1 second, more preferably at least 2 seconds, even more preferably at least 3 seconds, and is generally at most 10 hours, preferably at most 7 hours, more preferably at most 5 hours, even more preferably at most 3 hours, still more preferably at most 1 hour.

In the case where a solvent is not added to the liquid that contains an Si compound, the concentration of the Si compound therein is generally higher than in the case where a solvent is added thereto, and therefore, in general, the silylation may be attained at a lower temperature, taking a shorter period of time.

The pressure during the silylation treatment is not specifically defined. The silylation may be carried out under atmospheric pressure or sufficiently under autogenous pressure that would arise in heating the treatment solution put in a closed container within the above-mentioned temperature range. Further if desired, an inert gas such as nitrogen or the like may be added to the container.

In the case where the silylation is attained without addition of solvent and when the zeolite membrane composite is immersed in a liquid containing an Si compound and when the zeolite membrane composite is a tubular one, it is desirable that the bottom thereof alone or both the top and the bottom thereof are sealed up with a silicon rubber stopper or with a Teflon® tape or the like to thereby prevent a large amount of the Si compound and the Al compound from penetrating into the support. In that manner, the Si compound and the Al compound are brought into contact with the surface alone of the zeolite membrane while kept prevented from penetrating into the support part, and as a result, the zeolite membrane surface could be efficiently silylated at a high permeation kept as such.

In the case where the silylation is carried out without addition of any solvent, the zeolite membrane composite may be heated after immersed in a liquid, sol or gel at least containing the above-mentioned Si element source, for example, the Si compound. The heating temperature is generally 30° C. or higher, preferably 50° C. or higher, more preferably 70° C. or higher, and is generally 300° C. or lower, preferably 250° C. or lower, more preferably 200° C. or lower, even more preferably 150° C. or lower. When the temperature is not lower than the above-mentioned lower limit, then the modification of the zeolite membrane surface with the Si compound and the Al compound could be fully fixed. When the temperature is not higher than the upper limit, then Si—OH formed through modification would not be condensed to give an Si—O—Si bond, or that is, the hydrophilicity of the membrane surface could be sufficiently high.

In case where the system is heated after immersion, the heating time is generally at least 30 minutes, preferably at least 1 hour, more preferably at least 1.5 hours, even more preferably at least 2 hours, and is generally at most 30 hours, preferably at most 25 hours, even more preferably at most 20 hours, still more preferably at most 15 hours. When the time is not shorter than the above-mentioned lower limit, then the modification of the zeolite membrane surface with the Si compound and the Al compound could be fully fixed. When the time is not longer than the upper limit, then the system could be heated within a range within which the modification with the Si compound and the Al compound could be fully fixed, which is therefore advantageous in point of energy saving.

When the system is heated after immersion, water may be made to be present in the system to be heated. Water existing in the system could facilitate the hydrolysis of the alkoxysilanes and others contained in the silicate oligomer, and therefore the zeolite membrane surface could be fully modified with ease.

The heating after immersion may be carried out by the use of a drying machine, or the membrane after immersion may be put into a closed container and heated therein. When the membrane after immersion is put into a closed container, a small amount of water may be added thereto so as not to be brought into contact with the membrane.

For obtaining the zeolite membrane composite of the invention, the silylation treatment must be carried out under a suitable condition. For the silylation treatment, examples of especially preferred methods are the following (1) and (2). However, the method for producing the zeolite membrane composite of the invention are not limited to the following (1) and (2).

(1) A silylation method using an alkoxysilane such as tetraethoxysilane, tetramethoxysilane, methyltriethoxysilane, 3-aminopropyltriethoxysilane or the like as the Si compound.

It is important that water is used as the solvent for the solution to be used for silylation and the concentration of the alkoxysilane in the solution is suitably controlled within a predetermined range, and in accordance with it, the concentration of the acid or the base as well as the reaction temperature and others are controlled in a well-balanced manner.

The content of the Si compound in the solution is, as the concentration of the Si element therein, generally at least 0.01% by mass, preferably at least 0.05% by mass, more preferably at least 0.1% by mass, and is generally at most 10% by mass, preferably at most 5% by mass, more preferably at most 2% by mass.

In the solution, an acid or a base is preferably made to be present. As the acid, for example, preferred are carboxylic acids and inorganic acids. As the carboxylic acid, for example, preferred are formic acid, acetic acid, propionic acid, oxalic acid, malonic acid, maleic acid, phthalic acid, lactic acid, citric acid, acrylic acid, etc.; more preferred are formic acid, acetic acid and lactic acid; and especially preferred is acetic acid. As the inorganic acid, for example, preferred are sulfuric acid, nitric acid, phosphoric acid and hydrochloric acid; and more preferred are sulfuric acid, nitric acid and phosphoric acid. The concentration of the acidic substance in the aqueous solution is preferably at least 0.01 mol/l, more preferably at least 0.05 mol/l, even more preferably at most 10 mol/l, especially preferably at most 1 mol/l. As the base, for example, preferred are basic substances such as NaOH, KOH, amines, etc. The $OH^{-1}$ ion concentration in the aqueous solution is generally at most 0.01 mol/l, more preferably at most 0.005 mol/l, and is generally at least 0.0001 mol/l, preferably at least 0.0005 mol/l, more preferably at least 0.001 mol/l. The temperature of the solution is generally 20° C. or higher, preferably 60° C. or higher, more preferably 80° C. or higher, and is generally 200° C. or lower, preferably 150° C. or lower, more preferably 130° C. or lower. The time of immersion in the solution is generally at least 1 hour, preferably at least 4 hours, more preferably at least 8 hours, and is generally at most 100 hours, preferably at most 50 hours, more preferably at most 24 hours. The pressure during the silylation treatment is not specifically defined. The silylation may be carried out under atmospheric pressure or sufficiently under autogenous pressure that would arise in heating the treatment solution put in a closed container within the above-mentioned temperature range.

(2) A silylation method using a silicate oligomer as the Si compound.

A solvent may not be further added to the silicate oligomer, but a nonpolar solvent such as toluene, hexane or the like, anisole, an alcohol solvent such as isopropyl alcohol or the like, or a polar solvent such as acetone or the like may be added thereto. In the case where a solvent is added for immersion, the content of the Si compound in the solution is, as the concentration of the Si element therein, generally at least 0.1% by mass and preferably at least 1% by mass. The immersion temperature in the case of silylation treatment is generally not lower than 1° C., preferably not lower than 5° C., more preferably not lower than 10° C., even more preferably not lower than 15° C., and is generally not higher than 200° C., preferably not higher than 150° C., more preferably not higher than 130° C., even more preferably not higher than 100° C., most preferably not higher than 80° C. In this method, the immersion time and the heating treatment after immersion are important. The immersion time is generally at least 0.5 seconds, preferably at least 1 second, more preferably at least 2 seconds, even more preferably at least 3 seconds, and is generally at most 10 hours, preferably at most 7 hours, more preferably at most 5 hours, even more preferably at most 3 hours, especially preferably at most 1 hour. In the case of immersion with a solvent added to the system, the immersion time may be the same as that in the case of addition of no solvent thereto. In the case where the zeolite membrane composite is immersed in a liquid containing an Si compound and when the zeolite membrane composite is a tubular one, it is desirable that the bottom thereof alone or both the top and the bottom thereof are sealed up with a silicon rubber stopper or with a Teflon® tape or the like to thereby prevent a large amount of the Si compound and the Al compound from penetrating into the support. In the case where a silicate oligomer is used, preferred is heating after immersion. The heating temperature is generally 30° C. or higher, preferably 50° C. or higher, more preferably 70° C. or higher, and is generally 300° C. or lower, preferably 250° C. or lower, more preferably 200° C. or lower, even more preferably 150° C. or lower. In the case of heating after immersion, the heating time is generally at least 30 minutes, preferably at least 1 hour, more preferably at least 1.5 hours, even more preferably at least 2 hours, and is generally at most 30 hours, preferably at most 25 hours, more preferably at most 20 hours, even more preferably at most 15 hours. In the case of heating after immersion, preferably, water is made to be present in the system to be heated, and for example, when air is used as the atmosphere to be heated, water generally existing in air would be enough, but the temperature may be further elevated. The heating after immersion may be carried out by the use of an ordinary drying oven, or the membrane after immersion may be put into a closed container and heated therein. When the membrane after immersion is put into a closed container, preferably, a small amount of water is added thereto so as not to be brought into contact with the membrane.

Thus produced, the zeolite membrane composite has excellent properties as described above, and is favorably usable as the membrane separation means in the separation or concentration method of the invention.

<Separation or Concentration Method>

The separation of concentration method of the invention comprises bringing a gas or liquid mixture of multiple components into contact with the above-mentioned porous support-zeolite membrane composite to thereby separate the highly-permeative substance through permeation from the mixture. In addition, another characteristic feature of the method is that the poorly-permeative substance is concentrated through permeation of the highly-permeative substance from the mixture. In the invention, the porous support-zeolite membrane composite to be used may be the same as that mentioned above. Preferred embodiments thereof are also the same as those mentioned above.

According to the separation and concentration of the invention, a gas or liquid mixture of multiple components is brought into contact with the zeolite membrane via the inorganic porous support provided with the zeolite membrane, on one side of the support side or the zeolite membrane side and the pressure on the opposite side is kept lower than the pressure on the side that is kept in contact with the mixture, whereby the substance highly permeative through the zeolite membrane (the substance having a relatively high permeability in the mixture) is selectively, or that is, as the main component of the permeative substance, made to pass through the membrane. Therefore, the substance having a high permeability can be separated from the mixture. As a result, the concentration of a specific component in the mixture (substance having a relatively low permeability in the mixture) is increased to thereby separate and recover, or concentrate the specific component.

Not specifically defined, the mixture to be targeted for separation or concentration may be any gas or liquid mixture of multiple components capable of being separated or concentrated through the porous support-zeolite membrane composite of the invention.

In case where the mixture to be targeted for separation or concentration is, for example, a mixture of an organic compound and water (hereinafter this may be abbreviated as "water-containing organic compound"), in general, water is highly permeative through the zeolite membrane, and therefore water is separated from the mixture and the organic compound is concentrated in the original mixture. A separation or concentration method that is referred to as a pervaporation method or a vapor permeation method is one embodiment of the method of the invention. The pervaporation method is a separation or concentration method that comprises introducing a liquid mixture into the separation membrane directly as it is, and therefore facilitates the process including separation or concentration.

The vapor permeation method is a separation/concentration method in which a liquid mixture is vaporized and then introduced into the separation membrane, and which therefore enables combined use with a distillation apparatus or is applicable to separation at a higher temperature and a higher pressure. In addition, in the vapor permeation method, a liquid mixture is, after vaporized, introduced into the separation membrane, and therefore in this, the influence of the impurities contained in the supply liquid as well as that of the substance therein to form an associate or an oligomer in a liquid state on the membrane can be reduced. The inorganic porous support-zeolite membrane composite obtained according to the invention can be favorably used in any method.

In case of high-temperature separation according to the vapor permeation method, in general, the separation performance lowers more when the temperature is higher or when the concentration of the poorly-permeative component in the mixture is higher, for example, in a mixture of an organic compound and water, when the concentration of the organic compound is higher; however, the inorganic porous support-zeolite membrane composite obtained according to the invention can express high separation performance even at a high temperature and even when the concentration of the poorly-permeative component in the mixture is high. With that, in general, in the vapor permeation method, the liquid mixture is first vaporized and then separated, and therefore, in general, the separation condition is severer than in the pervaporation method, and accordingly, the vapor permeation method requires durability of the membrane composite to be used therein. The inorganic porous support-zeolite membrane composite obtained according to the invention has durability enough for separation even under high-temperature condition, and is therefore favorable for the vapor permeation method.

The porous support-zeolite membrane composite has specific physicochemical properties, and therefore not only in the case where the concentration of the poorly-permeative component in a mixture is high but also in the case where the concentration of the poorly-permeative component therein is low, the membrane composite can exhibit high permeation performance and selectivity, therefore securing the performance as a separation membrane excellent in durability. For example, in the case of a mixture of an organic compound and water, the membrane composite exhibits high selectivity irrespective of the concentration of water. Specifically, the zeolite membrane composite having specific physicochemical properties of the invention is favorable for separation and concentration of a mixture having a broad concentration range.

Here, the high permeation performance indicates a sufficient amount of throughput, and for example, means that the permeation flux of the substance to pass through the membrane is, when, for example, a mixture of acetic acid and water having a water content of 10% by mass is permeated through the membrane at 90° C. and under a pressure difference of 1 atmosphere ($1.01 \times 10^5$ Pa), at least 0.5 kg/(m²·hr), preferably at least 1 kg/(m²·hr), more preferably at least 1.5 kg/(m²·hr). The upper limit of the permeation flux is not specifically defined, and may be generally at most 20 kg/(m²·hr), preferably at most 15 kg/(m²·hr).

On the other hand, the above means that, when a mixture of phenol and water having a water content of 10% by mass is permeated through the membrane at 75° C. and under a pressure difference of 1 atmosphere ($1.01 \times 10^5$ Pa), the permeation flux of the substance to pass through the membrane is at least 0.5 kg/(m²·hr), preferably at least 1 kg/(m²·hr), more preferably at least 3 kg/(m²·hr). The upper limit of the permeation flux is not specifically defined, and may be generally at most 30 kg/(m²·hr), preferably at most 20 kg/(m²·hr).

Further, the above means that, when a mixture of 2-propanol or n-methyl-2-pyrrolidone and water having a water content of 30% by mass is permeated through the membrane at 70° C. and under a pressure difference of 1 atmosphere ($1.01 \times 10^5$ Pa), the permeation flux is at least 1 kg/(m²·hr), preferably at least 3 kg/(m²·hr), more preferably at least 5 kg/(m²·hr). The upper limit of the permeation flux is not specifically defined, and may be generally at most 20 kg/(m²·hr), preferably at most 15 kg/(m²·hr).

High permeation performance may be expressed in terms of permeance (also referred to as permeability). Permeance indicates a permeation flux per pressure difference (pressure normalized flux), and is a value to be obtained by dividing the permeated substance amount by the product of the membrane area, the time and the water partial pressure difference. In the case of expression in terms of permeance, for example, when a mixture of acetic acid and water having a water content of 10% by mass is permeated under a pressure difference of 1 atmospheric pressure ($1.01 \times 10^5$ Pa) at 90° C., the water permeance is generally at least $3 \times 10^{-7}$ mol/(m²·s·Pa), preferably at least $5 \times 10^{-7}$ mol/(m²·s·Pa), more preferably at least $1 \times 10^{-6}$ mol/(m²·s·Pa). The upper limit of the permeance is not specifically defined, and is generally at most $1 \times 10^{-4}$ mol/(m²·s·Pa), preferably at most $5 \times 10^{-5}$ mol/(m²·s·Pa).

When a mixture of phenol and water having a water content of 10% by mass is permeated under a pressure difference of 1 atmospheric pressure ($1.01 \times 10^5$ Pa) at 75° C., and when a mixture of 2-propanol or N-methyl-2-pyrrolidine and water having a water content of 30% by mass is permeated under a pressure difference of 1 atmospheric pressure ($1.01 \times 10^5$ Pa) at 70° C., the water permeance is generally at least $3 \times 10^{-7}$ mol/(m²·s·Pa), preferably at least $5 \times 10^{-7}$ mol/(m²·s·Pa), more preferably at least $1 \times 10^{-6}$ mol/(m²·s·Pa), even more preferably at least $2 \times 10^{-6}$ mol/(m²·s·Pa). The upper limit of the permeance is not specifically defined, and is generally at most $1 \times 10^{-4}$ mol/(m²·s·Pa), preferably at most $5 \times 10^{-5}$ mol/(m²·s·Pa).

The selectivity is represented by the separation factor. The separation factor is an index mentioned below to indicate the selectivity generally used in membrane separation.

$$\text{Separation Factor} = (P_\alpha/P_\beta)/(F_\alpha/F_\beta)$$

[wherein $P_\alpha$ indicates the mass percent concentration of the main component in the permeated liquid; $P_\beta$ indicates the mass percent concentration of the accessory component in the permeated liquid; $F_\alpha$ indicates the mass percent concentration of the component to be the main component in the permeated liquid, in the mixture to be separated; and $F_\beta$ indicates the mass percent concentration of the component to be the accessory component in the permeated liquid, in the mixture to be separated.]

The separation factor is, for example, when a mixture of acetic acid and water having a water content of 10% by mass is permeated under a pressure difference of 1 atmospheric pressure ($1.01 \times 10^5$ Pa) at 90° C., and for example, when a mixture of phenol and water having a water content of 10% by mass is permeated under a pressure difference of 1 atmospheric pressure ($1.01 \times 10^5$ Pa) at 75° C., and for example, when a mixture of 2-propanol or N-methyl-2-pyrrolidone and water having a water content of 30% by mass is permeated under a pressure difference of 1 atmospheric pressure ($1.01 \times 10^5$ Pa) at 70° C., generally at least 2000, preferably at least 4000, more preferably at least 10000, even more preferably at least 20000. The upper limit of the separation factor is in the case where entirely water only could pass through the membrane, and in the case, the separation factor would reach an infinite value, but the separation factor is preferably at most 10000000, more preferably at most 1000000.

The water-containing organic compound may be one in which the water content is previously controlled according to a suitable water content controlling method. The water content controlling method may be per se a known method, including, for example, distillation, pressure switching adsorption (PSA), temperature switching adsorption (TSA), desiccant system, etc.

Further, from the water-containing organic compound from which water has been separated through the zeolite membrane composite, water may be further separated. Accordingly, water can be separated highly, and the water-containing organic compound may be concentrated more highly.

The organic compound includes, for example, carboxylic acids such as acetic acid, acrylic acid, propionic acid, formic acid, lactic acid, oxalic acid, tartaric acid, benzoic acid, etc.; organic acids such as sulfonic acid, sulfinic acid, barbituric acid, uric acid, phenol, enol, diketone-type compounds, thiophenone, imide, oxime, aromatic sulfonamide, primary and secondary nitro compounds, etc.; alcohols such as methanol, ethanol, isopropanol (2-propanol), etc.; ketones such as acetone, methyl isobutyl ketone, etc.; aldehydes such as acetaldehyde, etc.; ethers such as dioxane, tetrahydrofuran, etc.; amides and other nitrogen-containing organic compounds (N-containing organic compounds) such as dimethylformamide, N-methylpyrrolidone, etc.; esters such as acetates, acrylates, etc.

Of those, in case where an organic acid is separated from a mixture of an organic acid and water based on the characteristics of both molecular sieve and hydrophilicity, the effect of the inorganic porous support-zeolite membrane composite is noticeably expressed. Preferred is a mixture of a carboxylic acid and water, and a more preferred example is separation of acetic acid from water.

In case where an organic substance and water are separated from a mixture of any other organic substance than an organic acid and water, the organic substance is preferably one having 2 or more carbon atoms, more preferably 3 or more carbon atoms.

Of those other organic substances than organic acids, especially preferred is an organic compound containing at least one selected from alcohols, ethers, ketones, aldehydes and amides. Of the organic compounds, preferred are those having from 2 to 10 carbon atoms, and more preferred are those having from 3 to 8 carbon atoms.

The organic compound may also be a polymer compound capable of forming a mixture with water (mixed solution).

The polymer compound includes those having a polar group in the molecule, for example, polyols such as polyethylene glycol, polyvinyl alcohol, etc.; polyamines; polysulfonic acids; polycarboxylic acids such as polyacrylic acid, etc.; polycarboxylic acid esters such as polyacrylic acid esters, etc.; modified polymer compounds prepared by modifying polymers through graft polymerization or the like; copolymerized polymer compounds prepared by copolymerization of a nonpolar monomer such as olefin or the like and a polar monomer having a polar group such as a carboxyl group, etc.

The water-containing organic compound may be a mixture capable of forming an azeotropic mixture, such as a mixture of water and phenol, and in separation of a mixture that forms an azeotropic mixture, the invention is advantageous in that water can be separated selectively and more efficiently than in separation by distillation. Concretely, there are mentioned a mixture of an alcohol such as ethanol, 1-propanol, 2-propanol, 1-butanol, 2-butanol or the like, and water; a mixture of an ester such as ethyl acetate, ethyl acrylate, methyl methacrylate or the like, and water; a mixture of a carboxylic acid such as formic acid, isobutyric acid, valeric acid or the like, and water; a mixture of an aromatic organic substance such as phenol, aniline or the like, and water; a mixture of a nitrogen-containing compound such as acetonitrile, acrylonitrile or the like, and water, etc.

Further, the water-containing organic compound may also be a mixture of water and a polymer emulsion. Here, the polymer emulsion is a mixture of a surfactant and a polymer that is generally used in adhesives, coating materials, etc. The polymer for use in the polymer emulsion includes, for example, thermoplastic resins, such as polyvinyl acetate, polyvinyl alcohol, acrylic resin, polyolefin, olefin-polar monomer copolymer such as ethylene-vinyl alcohol copolymer or the like, polystyrene, polyvinyl ether, polyamide, polyester, cellulose derivative, etc.; thermosetting resins such as urea resin, phenol resin, epoxy resin, polyurethane, etc.; rubbers such as natural rubber, polyisoprene, polychloroprene, butadiene copolymer such as styrene-butadiene copolymer or the like, etc. As the surfactant, herein employable is any per-se known one.

In the method of the invention, the mixture to be targeted for separation or concentration may be a gas mixture of multiple components. The gas mixture includes, for example, those containing at least one component selected from carbon dioxide, hydrogen, oxygen, nitrogen, methane, ethane, ethylene, propane, propylene, normal butane, isobutane, 1-butene, 2-butene, isobutene, sulfur hexafluoride, helium, carbon monoxide, nitrogen monoxide, water, etc. Of the mixtures comprising such gas components, the gas component having a high permeance is separated, after having passed through the zeolite membrane composite, while the gas component having a low permeance is concentrated on the supply gas side.

More preferably, the gas mixture contains at least two components of the above-mentioned components. In this case, the two components are preferably a combination of a component having a high permeance and a component having a low permeance.

For the condition of separation and concentration of the gas mixture (gas), employable is any per-se known condition in accordance with the gaseous species and the composition to be targeted.

The zeolite membrane composite of the invention has acid resistance, and therefore can be effectively utilized especially for separation of water from a mixture of water and an organic acid such as acetic acid or the like or for separation of water for promoting esterification.

The separation or concentration method of the invention may be carried out by producing a suitable separation or concentration apparatus by the use of the above-mentioned zeolite membrane composite, and introducing a gas or liquid mixture of multiple components into the apparatus. The separation or concentration apparatus can be produced by the use of per-se known members.

EXAMPLES

The invention is described more concretely, based on the following Experimental Examples (Examples, Comparative Examples); however, not overstepping the gist thereof, the invention is not limited by the following Experimental Examples. The production conditions and the data of the evaluation results in the following Examples have implications of preferred data in a range of the upper limit or the lower limit in the embodiments of the invention, and the preferred range may be one to be defined by the combination of the upper or lower limit and the data in the following Examples or by the combination of the data themselves in the following Examples.

<Measurement of Physical Data and Separation Performance>

In the following Experimental Examples, the physical properties and the separation performance were, unless otherwise specifically indicated, measured as follows:

(1) X-Ray Diffractometry (XRD)

For zeolite membrane XRD, the conditions are as mentioned below.
Apparatus: Netherlands PANaltical's X' PertPro MPD
Optical System Specification:
Incidence Side Encapsulated X-ray tube (CuKα)
 Soller Slit (0.04 rad)
 Divergence Slit (Variable Slit)
Stage: XYZ stage
Light-Receiving Side: Semiconductor array detector (X' Celerator)
 Ni-Filter
 Soller Slit (0.04 rad)
Goniometer Radius: 240 mm
Measurement Condition
X-ray Output (CuKα): 45 kV, 40 mA
Scanning Axis: θ/2θ
Scanning Range (2θ): 5.0 to 70.0°
Measurement Mode Continuous
Reading Width: 0.05°
Counting Time: 99.7 sec
Automatic Variable Slit (Automatic-DS):
 1 mm (irradiation width)
Horizontal Diffusion Mask: 10 mm (irradiation width)

X-ray is applied in the direction vertical to the axial direction of the cylindrical tube. Application of X-ray is so controlled that that X-ray could hit mainly on the other line above the surface of the stage, but not on the surface of the stage in the two lines kept in contact with both the cylindrical tubular membrane composite put on the stage and the plane parallel to the surface of the stage, in order to prevent noise and others as much as possible.

During the measurement, the irradiation width is fixed to be 1 mm by the use of the automatic variable slit, and using Materials Data Inc.'s XRD analysis software, JADE 7.5.2 (Japanese version), the XRD pattern is obtained through variable slit fixed slit conversion.

(2) Air Permeation Flux

One end of the zeolite membrane composite is sealed up and the other end is connected to a vacuum line at 5 kPa in a closed state, and the air flow rate is measured with the mass flow meter installed between the vacuum line and the zeolite membrane composite to give the air permeation flux[L/(m²·h)]. As the mass flow meter, used here is KOFLOC's Model 8300, for $N_2$ gas with a maximum flow rate of 500 ml/min (as a value at 20° C. and 1 atmospheric pressure). When the indication on the mass flow meter in KOFLOC's Model 8300 is not more than 10 ml/min (as a value at 20° C. and 1 atmospheric pressure), Lintec's MM-2100M is used, which is for air gas with a maximum flow rate of 20 ml/min (as a value at 0° C. and 1 atmospheric pressure).

(3) SEM Measurement

For SEM measurement, the conditions are as mentioned below.
Apparatus: SEM: FE-SEM Hitachi: S-4100
Accelerating Voltage: 10 kV (4) SEM-EDX Measurement For zeolite membrane SEM-EDX, the conditions are as mentioned below.

Apparatus: SEM: FE-SEM Hitachi: S-4800
 EDX: EDAX Genesis
Accelerating Voltage: 10 kV X-Ray quantitative analysis was performed by scanning the entire surface of visual field (25 μm×18 μm) at a magnification of 5,000 times.

Through SEM-EDX, the molar ratio of $SiO_2/Al_2O_3$ in the formed zeolite membrane itself is determined. SEM-EDX in which the X-ray irradiation energy is 10 kV or so provides some information of the zeolite membrane alone having a thickness of a few microns.

(5) XPS Measurement

The zeolite membrane surface is analyzed through XPS (X-ray photoelectron spectroscopy) under the conditions mentioned below.
Apparatus: PHI's Quantum 2000
X-ray Source: Monochromatic Al—Kα, output 16 kV-34 W (X-ray generation area 170 μmφ)
Electrification Neutralization Combined use of electronic gun (5μ) and ionic gun (10 V).
Spectroscopic System:
 Pulse energy 187.85 eV @ wide spectrum
 58.70 eV @ narrow spectrum (Na1s, Al2p, Si2p, K2p, S2p)
 29.35 eV @ wide spectrum (C1s, O1s, Si2p)
Measurement Region: spot irradiation (irradiation area<340 μmφ)
Takeoff Angle: 45° (from surface)

From the data of XPS, obtained is the molar ratio of $SiO_2/Al_2O_3$ in the formed zeolite membrane surface.

(6) Pervaporation

FIG. 1 shows an outline view of the apparatus used for pervaporation. In FIG. 1, the inside area of the zeolite membrane composite 5 is depressurized via the vacuum pump 9 so that the pressure difference between the inside of the composite and the outside thereof kept in contact with the sample liquid 4 to be separated could be about 1 atmospheric pressure. The internal pressure is measured with the Pirani gauge 6. Owing to the pressure difference, the permeative substance, water in the sample liquid 4 to be separated is pervaporated and permeates the zeolite membrane composite 5. The permeated substance is trapped by the permeated liquid collecting trap 7, while the substance not trapped by the permeated liquid collecting trap 7, if any, is trapped by the cold trap 8. On the other hand, the organic compound in the sample liquid 4 to be separated is left to remain outside the zeolite membrane composite 5. The sample liquid to be separated is heated up to a predetermined temperature by the hot bath 2, and is stirred with stirring blade 3 that is rotated by the stirrer 1.

At regular time intervals, the permeated liquid trapped by the permeated liquid collecting trap 7 is analyzed for mass measurement and compositional analysis, and the sample liquid 4 to be separated was analyzed for the composition thereof. Using the thus-found data, the separation factor, the permeation flux and the water permeance at each time are calculated as described above. For composition analysis, employed is gas chromatography.

(7) Vapor Permeation

FIG. 2 shows an outline view of the apparatus used for vapor permeation. In FIG. 2, the sample liquid 10 to be separated is fed to the vaporizer 12 via the feeding pump 11, at a predetermined flow rate, and is entirely vaporized by heating in the vaporizer 12 to be a gas to be separated. The gas to be separated is introduced into the zeolite membrane composite module 14 in the thermostat bath 13, and is supplied in the space outside of the zeolite membrane composite. The zeolite membrane composite module 14 is constructed by housing the zeolite membrane composite in a housing. The inside area of the zeolite membrane composite is depressurized by the vacuum pump 18 so that the pressure difference between the inside area thereof and the gas to be separated could be about 1 atmospheric pressure. The internal pressure can be measured with a Pirani gauge though not shown. Owing to the pressure difference, the permeative substance, water in the gas to be separated Zeolite membrane composite. The permeated substance is trapped by the permeated liquid collecting trap 16, while the substance not trapped by the permeated liquid collecting trap 16, if any, is trapped by the cold trap 17. On the other hand, the component not permeated but left in the gas to be separated is liquefied and collected in the collecting trap 15 of liquid to be separated.

At regular time intervals, the permeated liquid trapped by the permeated liquid collecting trap 16 is analyzed for mass measurement and compositional analysis. Using the thus-found data, the separation factor, the permeation flux and the water permeance at each time are calculated as described above. For composition analysis, employed is gas chromatography.

(8) Water Vapor Adsorption Isotherm

Using an adsorption isotherm measuring apparatus (BELSORP 18, by BEL Japan), the water vapor adsorption isotherm at 35° C. is measured. The zeolite membrane composite is previously cut into a suitable size that can be put in the measurement cell. While degassed in vacuum, the sample is heated and dried at 120° C. for 5 hours, and then used for the measurement. Regarding the measurement condition, the air thermostat bath temperature is 50° C., the adsorption temperature is 35° C., the initial introduction pressure is 3 Torr ($4.00 \times 10^2$ Pa), the saturation vapor pressure is 42.181 Torr ($56.237 \times 10^2$ Pa), and the equilibrium time is 500 seconds.

From the found data, the water adsorption (g) per gram of the CHA-type zeolite membrane composite at a relative pressure of 0.8 is obtained.

Comparative Example 1

An inorganic porous support-CHA-type zeolite membrane composite was produced through direct hydrothermal synthesis of a CHA-type zeolite on an inorganic porous support, as described below.

As a reaction mixture for hydrothermal synthesis, the following was prepared.

0.88 g of aluminium hydroxide (containing 53.5% by mass of $Al_2O_3$, by Aldrich) was added to a mixture of 10.5 g of aqueous 1 mol/L-NaOH solution, 7.0 g of aqueous 1 mol/L-KOH solution and 100.5 g of water, and dissolved by stirring to give a transparent solution. As an organic template, 2.36 g of an aqueous solution of N,N,N-trimethyl-1-adamantanammonium hydroxide (hereinafter this is referred to as "TMADAOH") (containing 25% by mass of TMADAOH, by SACHEM) was added to the above, and further 10.5 g of colloidal silica (Nissan Chemical's Snowtec-40) was added thereto, and stirred for 2 hours to give a reaction mixture.

The composition (ratio by mol) of the reaction mixture is $SiO_2/Al_2O_3/NaOH/KOH/H_2O/TMADAOH=1/0.066/0.15/0.1/100/0.04$, and $SiO_2/Al_2O_3=15$.

As an inorganic porous support, a mullite tube PM by Nikkato (outer diameter 12 mm, inner diameter 9 mm) was cut into a length of 80 mm, washed with an ultrasonic washing machine, dried and then used here.

As a seed crystal, used here was a CHA-type zeolite that had been prepared to have a gel composition (ratio by mol) of $SiO_2/Al_2O_3/NaOH/KOH/H_2O/TMADAOH=1/0.033/0.1/0.06/40/0.07$, through hydrothermal synthesis for crystallization at 160° C. for 2 hours. The grain size of the seed crystal was 1 µM or so.

The seed crystal was dispersed in water at 1% by mass, and the above-mentioned support was dipped in the resulting dispersion for a predetermined period of time, and thereafter dried at 100° C. for 5 hours to thereby make the seed crystal adhere to the support. The mass of the thus-adhering seed crystal was 0.9 g/m².

The support to which the seed crystal had adhered was immersed in the reaction mixture put in a Teflon®-made inner cylinder (200 ml), in the vertical direction therein, and the autoclave was sealed up, and while kept static therein, this was heated at 160° C. for 48 hours under autogenous pressure. After a predetermined period of time, this was left cooled and the support-zeolite membrane composite was taken out of the reaction mixture, then washed and dried at 100° C. for 5 hours or more.

The zeolite membrane composite in which the template was not as yet calcined, was calcined in an electric furnace at 500° C. for 5 hours. The mass of the CHA-type zeolite crystallized on the support, which was obtained from the difference between the mass of the membrane composite after calcined and the mass of the support, was 130 g/m².

The permeation flux of air through the calcined zeolite membrane composite was 60 L/(m²·hr).

XRD of the formed membrane confirmed the formation of CHA-type zeolite therein.

In the XRD pattern, (peak intensity at around $2\theta=17.9°$)/(peak intensity at around $2\theta=20.8°$)=3.5, or that is, the peak intensity at around $2\theta=17.9°$ is significantly large as compared with that in XRD of the powdery CHA-type zeolite used as the seed crystal, from which the orientation to the (1,1,1) plane in rhombohedral setting is assumed.

SEM data of the inorganic porous support-CHA-type zeolite membrane composite confirmed the crystals densely formed on the surface of the composite.

The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 36.2. The difference between the molar ratio of $SiO_2/Al_2O_3$ in the zeolite membrane itself and the molar ratio of $SiO_2/Al_2O_3$ in the membrane surface was not more than 20.

Using the obtained inorganic porous support-CHA-type zeolite membrane composite, water was selectively separated through pervaporation from a mixed solution of water/acetic acid (5/95 mass %) at 90° C.

After 5.5 hours, the permeation result was as follows. The permeation flux was 1.3 kg/(m²·hr); the separation factor was 400, and the water concentration in the permeated liquid was 95.75% by mass. The water permeance is $1.5 \times 10^{-6}$ mol/(m²·sec·Pa).

Example 1

An inorganic porous support-CHA-type zeolite membrane composite was produced under the same condition as in Comparative Example 1. The zeolite membrane composite was put in a Teflon®-made inner cylinder, as immersed in 135 g of desalted water, 2.5 g of tetraethoxysilane (hereinafter this may be abbreviated as "THOS") and 1.4 g of sulfuric acid in the vertical direction therein, then the autoclave was sealed up, and heated at 100° C. for 20 hours under autogenous pressure. After a predetermined period of time, this was left cooled and the zeolite membrane composite was taken out and washed with desalted water. Hereinafter this treatment is referred to as "silylation treatment 1". The pH of the processing solution used in the silylation treatment 1 was 1.0, the $H^+$ concentration thereof was 0.1 mol/l, and the Si content thereof was 0.24% by mass.

After processed for the silylation treatment 1, the zeolite membrane composite was analyzed through SEM-EDX, in which the molar ratio of $SiO_2/Al_2O_3$ in the zeolite membrane itself was 19, and was analyzed through XPS, in which the molar ratio of $SiO_2/Al_2O_3$ in the zeolite membrane surface was 109.8. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 1, the inorganic porous support-CHA-type zeolite membrane composite that had been processed for the silylation treatment 1 was used for selective permeation and separation of water from a mixed solution of water/acetic acid (5/95 mass %) at 90° C. through pervaporation.

After 5 hours, the permeation result was as follows. The permeation flux was 0.92 kg/($m^2$·hr); the separation factor was 17900, and the water concentration in the permeated liquid was 99.89% by mass. The water permeance is 1.2× $10^{-6}$ mol/($m^2$·sec·Pa).

From the results in Comparative Example 1 and Example 1, it is known that the separation factor increased by 45 times by increasing the molar ratio of $SiO_2/Al_2O_3$ in the zeolite membrane surface to be larger by at least 20 than the molar ratio of $SiO_2/Al_2O_3$ in the zeolite membrane itself.

Example 2

An inorganic porous support-CHA-type zeolite membrane composite was produced under the same condition as in Comparative Example 1. The zeolite membrane composite was put in a Teflon®-made inner cylinder, as immersed in 135 g of desalted water, 2.5 g of tetraethoxysilane (TEOS) and 1.62 g of acetic acid in the vertical direction therein, then the autoclave was sealed up, and heated at 100° C. for 20 hours under autogenous pressure. After a predetermined period of time, this was left cooled and the zeolite membrane composite was taken out and washed with desalted water. Hereinafter this treatment is referred to as "silylation treatment 2". The pH of the processing solution used in the silylation treatment 2 was 2.9, the $H^+$ concentration thereof was 0.001 mol/l, and the Si content thereof was 0.24% by mass.

After processed for the silylation treatment 2, the zeolite membrane composite was analyzed through SEM-EDX, in which the molar ratio of $SiO_2/Al_2O_3$ in the zeolite membrane itself was 15, and was analyzed through XPS, in which the molar ratio of $SiO_2/Al_2O_3$ in the zeolite membrane surface was 91.2. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 1, the inorganic porous support-CHA-type zeolite membrane composite that had been processed for the silylation treatment 2 was used for selective permeation and separation of water from a mixed solution of water/acetic acid (5/95 mass %) at 90° C. through pervaporation.

After 5 hours, the permeation result was as follows. The permeation flux was 1.2 kg/($m^2$·hr); the separation factor was 210000, and the water concentration in the permeated liquid was 99.99% by mass. The water permeance is 1.7× $10^{-6}$ mol/($m^2$·sec·Pa).

From the results in Comparative Example 1 and Example 2, it is known that the separation factor increased by 500 times by increasing the molar ratio of $SiO_2/Al_2O_3$ in the zeolite membrane surface to be larger by at least 20 than the molar ratio of $SiO_2/Al_2O_3$ in the zeolite membrane itself.

Comparative Example 2

An inorganic porous support-CHA-type zeolite membrane composite was produced under the same condition as in Comparative Example 1. The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 36.2. The difference between the molar ratio of $SiO_2/Al_2O_3$ in the zeolite membrane itself and the molar ratio of $SiO_2/Al_2O_3$ in the zeolite membrane surface was not more than 20.

Using the obtained inorganic porous support-CHA-type zeolite membrane composite, water was selectively separated through pervaporation from a mixed solution of water/acetic acid (10/90 mass %) at 90° C.

After 5 hours, the permeation result was as follows. The permeation flux was 1.8 kg/($m^2$·hr); the separation factor was 1900, and the water concentration in the permeated liquid was 99.49% by mass. The water permeance is 1.3× $10^{-6}$ mol/($m^2$·sec·Pa).

Example 3

An inorganic porous support-CHA-type zeolite membrane composite was produced under the same condition as in Comparative Example 1.

The zeolite membrane composite was put in a Teflon®-made inner cylinder, as immersed in 135 g of desalted water, 2.5 g of tetraethoxysilane (TEOS) and 4.7 g of phosphoric acid in the vertical direction therein, then the autoclave was sealed up, and heated at 100° C. for 20 hours under autogenous pressure. After a predetermined period of time, this was left cooled and the support-zeolite membrane composite was taken out and washed with desalted water. Hereinafter this treatment is referred to as "silylation treatment 3". The pH of the processing solution used in the silylation treatment 3 was 1.3, the $H^+$ concentration thereof was 0.05 mol/l, and the Si content thereof was 0.24% by mass.

After processed for the silylation treatment 3, the zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 90.0. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 1, the inorganic porous support-CHA-type zeolite membrane composite that had been processed for the silylation treatment 3 was used for selective permeation and separation of water from a mixed solution of water/acetic acid (10/90 mass %) at 90° C. through pervaporation.

After 5 hours, the permeation result was as follows. The permeation flux was 1.7 kg/(m²·hr); the separation factor was 99100, and the water concentration in the permeated liquid was 99.99% by mass. The water permeance is 1.3× $10^{-6}$ mol/(m²·sec·Pa).

From the results in Comparative Example 2 and Example 3, it is known that the separation factor increased by 52 times by increasing the molar ratio of $SiO_2/Al_2O_3$ in the zeolite membrane surface to be larger by at least 20 than the molar ratio of $SiO_2/Al_2O_3$ in the zeolite membrane itself.

Example 4

An inorganic porous support-CHA-type zeolite membrane composite was produced under the same condition as in Comparative Example 1. The zeolite membrane composite was put in a Teflon®-made inner cylinder, as immersed in 134 g of desalted water and 1.8 g of colloidal silica (Snowtex 40 by Nissan Chemical) in the vertical direction therein, then the autoclave was sealed up, and heated at 100° C. for 21 hours under autogenous pressure. After a predetermined period of time, this was left cooled and the zeolite membrane composite was taken out and washed with desalted water. Hereinafter this treatment is referred to as "silylation treatment 4". The Si content in the processing solution used for the silylation treatment 4 was 0.25% by mass.

After processed for the silylation treatment 4, the zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 43.6 The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 2, the inorganic porous support-CHA-type zeolite membrane composite that had been processed for the silylation treatment 4 was used for selective permeation and separation of water from a mixed solution of water/acetic acid (10/90 mass %) at 90° C. through pervaporation.

After 5 hours, the permeation result was as follows. The permeation flux was 2.3 kg/(m²·hr); the separation factor was 91000, and the water concentration in the permeated liquid was 99.99% by mass. The water permeance is 1.6× $10^{-6}$ mol/(m²·sec·Pa).

From the results in Comparative Example 2 and Example 4, it is known that the separation factor increased by 48 times by increasing the molar ratio of $SiO_2/Al_2O_3$ in the zeolite membrane surface to be larger by at least 20 than the molar ratio of $SiO_2/Al_2O_3$ in the zeolite membrane itself.

Comparative Example 3

An inorganic porous support-CHA-type zeolite membrane composite was produced under the same condition as in Comparative Example 1, except that a porous alumina tube (outer diameter 12 mm, inner diameter 9 mm) was used as the inorganic porous support. The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 32.4. The difference between the molar ratio of $SiO_2/Al_2O_3$ in the zeolite membrane itself and the molar ratio of $SiO_2/Al_2O_3$ in the zeolite membrane surface was not more than 20.

Using the obtained inorganic porous support-CHA-type zeolite membrane composite, water was selectively separated through pervaporation from a mixed solution of water/phenol (10/90 mass %) at 75° C. After 3 hours, the permeation result was as follows. The permeation flux was 5.8 kg/(m²·hr); the separation factor was 700, the water concentration in the permeated liquid was 98.78% by mass, and the phenol concentration was 1.22% by mass. The water permeance is 2.9×$10^{-6}$ mol/(m²·sec·Pa).

Example 5

An inorganic porous support-CHA-type zeolite membrane composite was produced under the same condition as in Comparative Example 3. The zeolite membrane composite was put in a Teflon®-made inner cylinder, as immersed in 135 g of desalted water, 2.5 g of tetraethoxysilane (TEOS) and 4.05 g of acetic acid in the vertical direction therein, then the autoclave was sealed up, and heated at 100° C. for 20 hours under autogenous pressure. After a predetermined period of time, this was left cooled and the support-zeolite membrane composite was taken out and washed with desalted water. Hereinafter this treatment is referred to as "silylation treatment 5". The pH of the processing solution used for the silylation treatment 5 was 2.8, the H⁺ concentration thereof was 0.0016 mol/l, the Si content thereof was 0.24% by mass.

After processed for the silylation treatment 5, the zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 60.4 The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 3, the inorganic porous support-CHA-type zeolite membrane composite that had been processed for the silylation treatment 5 was used for selective permeation and separation of water from a mixed solution of water/phenol (10/90 mass %) at 75° C. through pervaporation.

After 3 hours, the permeation result was as follows. The permeation flux was 5.2 kg/(m²·hr); the separation factor was 75500, the water concentration in the permeated liquid was 99.99% by mass, and the phenol concentration therein was 0.01% by mass. The water permeance is 2.7×$10^{-6}$ mol/(m²·sec·Pa).

From the results in Comparative Example 3 and Example 5, it is known that the separation factor increased by 100 times by increasing the molar ratio of $SiO_2/Al_2O_3$ in the zeolite membrane surface to be larger by at least 20 than the molar ratio of $SiO_2/Al_2O_3$ in the zeolite membrane itself.

Comparative Example 4

An inorganic porous support-CHA-type zeolite membrane composite was produced under the same condition as in Comparative Example 1. The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 36.2. The difference between the molar ratio of $SiO_2/Al_2O_3$ in the zeolite membrane itself and the molar ratio of $SiO_2/Al_2O_3$ in the zeolite membrane surface was not more than 20.

Using the obtained inorganic porous support-CHA-type zeolite membrane composite, water was selectively separated through vapor permeation from a mixed solution of water/acetic acid (10/90 mass %). The inorganic porous support-CHA-type zeolite membrane composite was set in a thermostat bath at 130° C., and the mixed solution of water/acetic acid was fed into a vaporizer at a flow rate of 0.8 cm³/min, wholly vaporized therein and applied to the inorganic porous support-CHA-type zeolite membrane composite.

After 2 hours, the permeation result was as follows. The permeation flux was 2.8 kg/(m²·hr); the separation factor was 5, and the water concentration in the permeated liquid was 34.92% by mass. The water permeance is $5.5 \times 10^{-7}$ mol/(m²·sec·Pa).

Example 6

An inorganic porous support-CHA-type zeolite membrane composite was produced under the same condition as in Comparative Example 1. The zeolite membrane composite was processed for the silylation treatment 1 in the same manner as in Example 1 and then heated at 170° C. for 1 hour.

After processed for the silylation treatment 1, the zeolite membrane composite was analyzed through SEM-EDX, in which the molar ratio of $SiO_2/Al_2O_3$ in the zeolite membrane itself was 19, and was analyzed through XPS, in which the molar ratio of $SiO_2/Al_2O_3$ in the zeolite membrane surface was 109.8 The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 4, the inorganic porous support-CHA-type zeolite membrane composite that had been processed for the silylation treatment 1 and then heated at 170° C. for 1 hour was used for selective permeation and separation of water from a mixed solution of water/acetic acid (10/90 mass %) through vapor permeation.

After 2 hours, the permeation result was as follows. The permeation flux was 0.88 kg/(m²·hr); the separation factor was 18000, and the water concentration in the permeated liquid was 99.95% by mass. The water permeance is $5.0 \times 10^{-7}$ mol/(m²·sec·Pa).

From the results in Comparative Example 4 and Example 6, it is known that the separation factor increased by 3600 times by increasing the molar ratio of $SiO_2/Al_2O_3$ in the zeolite membrane surface to be larger by at least 20 than the molar ratio of $SiO_2/Al_2O_3$ in the zeolite membrane itself.

Comparative Example 5

An inorganic porous support-CHA-type zeolite membrane composite was produced under the same condition as in Comparative Example 3. The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 32.4. The difference between the molar ratio of $SiO_2/Al_2O_3$ in the zeolite membrane itself and the molar ratio of $SiO_2/Al_2O_3$ in the zeolite membrane surface was not more than 20.

Using the obtained inorganic porous support-CHA-type zeolite membrane composite, water was selectively separated through vapor permeation from a mixed solution of water/acetic acid (10/90 mass %).

After 5 hours, the permeation result was as follows. The permeation flux was 1.4 kg/(m²·hr); the separation factor was 40, and the water concentration in the permeated liquid was 82.63% by mass. The water permeance is $6.3 \times 10^{-7}$ mol/(m²·sec·Pa).

Example 7

An inorganic porous support-CHA-type zeolite membrane composite was produced under the same condition as in Comparative Example 3. The zeolite membrane composite was put in an eggplant flask, as immersed in 135 g of toluene, 2.5 g of tetraethoxysilane (TEOS) and 2.66 g of 3-aminopropyltriethoxysilane (hereinafter this may be abbreviated as "APTS") therein, and then heated in a nitrogen stream atmosphere at 100° C. for 8 hours. After a predetermined period of time, the zeolite membrane composite was taken out and washed with acetone. Subsequently, this was heated at 170° C. for 2 hours. Hereinafter this treatment is referred to as "silylation treatment 6". The Si content in the processing solution used for the silylation treatment 6 was 0.48% by mass.

After processed for the silylation treatment 6, the zeolite membrane composite was analyzed through SEM-EDX, in which the molar ratio of $SiO_2/Al_2O_3$ in the zeolite membrane was 17, and was analyzed through XPS, in which the molar ratio of $SiO_2/Al_2O_3$ in the zeolite membrane surface was 146.4 The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 5, the inorganic porous support-CHA-type zeolite membrane composite that had been processed for the silylation treatment 6 was used for selective permeation and separation of water from a mixed solution of water/acetic acid (10/90 mass %) through vapor permeation.

After 5 hours, the permeation result was as follows. The permeation flux was 0.84 kg/(m²·hr); the separation factor was 500, and the water concentration in the permeated liquid was 98.15% by mass. The water permeance is $4.5 \times 10^{-7}$ mol/(m²·sec·Pa).

From the results in Comparative Example 5 and Example 7, it is known that the separation factor increased by 12 times by increasing the molar ratio of $SiO_2/Al_2O_3$ in the zeolite membrane surface to be larger by at least 20 than the molar ratio of $SiO_2/Al_2O_3$ in the zeolite membrane itself.

Example 8

An inorganic porous support-CHA-type zeolite membrane composite was produced in the same manner as in Comparative Example 1 except that a reaction mixture having a composition (ratio by mol) of $SiO_2/Al_2O_3$/NaOH/KOH/$H_2O$/TMADAOH=1/0.033/0.05/0.1/100/0.04 and $SiO_2/Al_2O_3$=30 was used for hydrothermal synthesis. The mass of the CHA-type zeolite crystallized on the support, as obtained from the difference between the mass of the membrane composite after calcined and the mass of the support, was 160 g/m².

The permeation flux of air through the calcined zeolite membrane composite was 50 L/(m²·hr).

XRD of the formed membrane confirmed the formation of CHA-type zeolite therein.

In the XRD pattern, (peak intensity at around 2θ=17.9°)/(peak intensity at around 2θ=20.8°)=0.53, or that is, the peak intensity at around 2θ=17.9° is significantly large as compared with that in XRD of the powdery CHA-type zeolite used as the seed crystal, from which the orientation to the plane (1,1,1) in rhombohedral setting is assumed.

SEM data of the zeolite membrane composite confirmed the crystals densely formed on the surface of the composite.

The obtained inorganic porous support-CHA-type zeolite membrane composite was processed for the silylation treatment 2.

The zeolite membrane composite processed for the silylation treatment 2 was analyzed through SEM-EDX, in which the molar ratio of $SiO_2/Al_2O_3$ in the zeolite membrane itself was 22, and was analyzed through XPS, in which the molar ratio or $SiO_2/Al_2O_3$ in the zeolite membrane surface was 44.2. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

Example 9

An inorganic porous support-CHA-type zeolite membrane composite was produced in the same manner as in Comparative Example 1 except that a reaction mixture having a composition (ratio by mol) of $SiO_2/Al_2O_3$/NaOH/KOH/$H_2O$/TMADAOH=1/0.02/0.05/0.1/100/0.05 and $SiO_2/Al_2O_3$=50 was used for hydrothermal synthesis. The mass of the CHA-type zeolite crystallized on the support, as obtained from the difference between the mass of the membrane composite after calcined and the mass of the support, was 160 g/m².

The permeation flux of air through the calcined zeolite membrane composite was 140 L/(m²·hr).

XRD of the formed membrane confirmed the formation of CHA-type zeolite therein.

In the XRD pattern, (peak intensity at around 2θ=17.9°)/(peak intensity at around 2θ=20.8°)=0.38, and (peak intensity at around 2θ=9.6°)/(peak intensity at around 2θ=20.8°) =3.8. The peak intensity at around 2θ=9.6° is large as compared with that in XRD of the powdery CHA-type zeolite used as the seed crystal, from which the orientation to the plane (1,0,0) in rhombohedral setting is assumed.

SEM data of the zeolite membrane composite confirmed the crystals densely formed on the surface of the composite.

The obtained inorganic porous support-CHA-type zeolite membrane composite was processed for the silylation treatment 2.

The zeolite membrane composite processed for the silylation treatment 2 was analyzed through SEM-EDX, in which the molar ratio of $SiO_2/Al_2O_3$ in the zeolite membrane was 28, and was analyzed through XPS, in which the molar ratio of $SiO_2/Al_2O_3$ in the zeolite membrane surface was 57.6. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

Comparative Example 6

An inorganic porous support-CHA-type zeolite membrane composite was produced under the same condition as in Comparative Example 1. A part of the obtained inorganic porous support-CHA-type zeolite membrane composite was analyzed to provide the water vapor adsorption isotherm thereof. The water adsorption per gram of the CHA-type zeolite membrane composite at a relative pressure of 0.8, as obtained from the water vapor adsorption isotherm, was 0.01423 g.

A part of the obtained inorganic porous support-CHA-type zeolite membrane composite was immersed in an aqueous 90 mass % acetic acid solution at room temperature for 1 week. The zeolite membrane composite was taken out of the liquid, and well washed with desalted water, and then in the same manner as above, analyzed to provide the water vapor adsorption isotherm thereof. The water adsorption per gram of the CHA-type zeolite membrane composite at a relative pressure of 0.8, as obtained from the water vapor adsorption isotherm, was 0.01135 g.

As above, the water adsorption of the CHA-type zeolite membrane composite after immersed in the aqueous 90 mass % acetic acid solution for 1 week decreased to 80% of the water adsorption thereof before immersion.

In the same manner as in Comparative Example 1, the obtained inorganic porous support-CHA-type zeolite membrane composite was used for selective permeation and separation of water from a mixed solution of water/acetic acid (10/90 mass %) at 90° C. through pervaporation.

After 5 hours, the permeation result was as follows. The permeation flux was 1.8 kg/(m²·hr); the separation factor was 1900, and the water concentration in the permeated liquid was 99.49% by mass. The water permeance is 1.3× $10^{-6}$ mol/(m²·sec·Pa).

Example 10

An inorganic porous support-CHA-type zeolite membrane composite was produced under the same condition as in Comparative Example 1. The zeolite membrane composite was processed for the silylation treatment 2.

A part of the inorganic porous support-CHA-type zeolite membrane composite that had been processed for the silylation treatment 2 was analyzed in the same manner as in Comparative Example 6 to provide the water vapor adsorption isotherm thereof. The water adsorption per gram of the CHA-type zeolite membrane composite at a relative pressure of 0.8, as obtained from the water vapor adsorption isotherm, was 0.01368 g.

In the same manner as in Comparative Example 6, a part of the inorganic porous support-CHA-type zeolite membrane composite that had been processed for the silylation treatment 2 was immersed in an aqueous 90 mass % acetic acid solution at room temperature for 1 week. The zeolite membrane composite was taken out of the liquid, and well washed with desalted water, and then in the same manner as above, analyzed to provide the water vapor adsorption isotherm thereof. The water adsorption per gram of the CHA-type zeolite membrane composite at a relative pressure of 0.8, as obtained from the water vapor adsorption isotherm, was 0.01275 g. After immersed in the aqueous 90 mass % acetic acid solution for 1 week, the water adsorption of the CHA-type zeolite membrane composite at a relative pressure of 0.8 was 93% of the water adsorption thereof before immersion.

In the same manner as in Comparative Example 1, the inorganic porous support-CHA-type zeolite membrane composite that had been processed for the silylation treatment 2 was used for selective permeation and separation of water from a mixed solution of water/acetic acid (10/90 mass %) at 90° C. through pervaporation.

After 5 hours, the permeation result was as follows. The permeation flux was 1.7 kg/(m²·hr); the separation factor was 96400, and the water concentration in the permeated liquid was 99.99% by mass. The water permeance is 1.3× $10^{-6}$ mol/(m²·sec·Pa).

From the results in Comparative Example 6 and Example 10, it is known that the CHA-type zeolite membrane composite, of which the water adsorption at a relative pressure 0.8 after immersed in an aqueous 90 mass % acetic acid solution for 1 week was more than 82% of the water adsorption thereof before immersion, has at least 50 times better separation performance.

The results in Comparative Example 6 and Example 10 are shown in Table 2.

Comparative Example 11

An inorganic porous support-CHA-type zeolite membrane composite was produced through direct hydrothermal synthesis of a CHA-type aluminosilicate zeolite on an inorganic porous support, as described below.

A reaction mixture for hydrothermal synthesis was prepared as follows:

0.306 g of aluminium hydroxide (containing 53.5% by mass of $Al_2O_3$, by Aldrich) was added to a mixture of 12.0 g of aqueous 1 mol/L-NaOH solution, 8.0 g of aqueous 1 mol/L-KOH solution and 115 g of water, and dissolved by stirring to give a transparent solution. As an organic template, 2.7 g of an aqueous solution of N,N,N-trimethyl-1-adamantanammonium hydroxide (hereinafter this is referred to as "TMADAOH") (containing 25% by mass of TMADAOH, by SACHEM) was added to the above, and further 12.0 g of colloidal silica (Nissan Chemical's Snowtec-40) was added thereto, and stirred for 2 hours to give a reaction mixture.

The composition (ratio by mol) of the reaction mixture is $SiO_2/Al_2O_3/NaOH/KOH/H_2O/TMADAOH=1/0.02/0.15/0.1/100/0.04$, and $SiO_2/Al_2O_3=50$.

As an inorganic porous support, a porous alumina tube (outer diameter 12 mm, inner diameter 9 mm) was cut into a length of 80 mm, washed with an ultrasonic washing machine, dried and then used here.

As a seed crystal, used here was a CHA-type zeolite precipitate that had been prepared to have a gel composition (ratio by mol) of $SiO_2/Al_2O_3/NaOH/KOH/H_2O/TMADAOH=1/0.066/0.15/0.1/100/0.04$, through hydrothermal synthesis at 160° C. for 2 hours in a porous alumina tube (outer diameter 12 mm, inner diameter 9 mm) followed by filtration, washing with water and drying. The grain size of the seed crystal was from 2 to 4 µm or so.

The seed crystal was dispersed in an aqueous alkali solution of 0.33 mass % NaOH and 0.31% KOH to be in an amount of about 1% by mass therein. The above-mentioned support was dipped in the dispersion for a predetermined period of time, and then dried at 100° C. for 4 hours or more to thereby make the seed crystal adhere to the support. After the drying, the mass increase was 8.3 g/m².

The support to which the seed crystal had adhered was immersed in the above-mentioned aqueous reaction mixture put in a Teflon®-made inner cylinder (200 ml) in the vertical direction therein, and the autoclave was sealed up, and while kept static therein, this was heated at 160° C. for 48 hours under autogenous pressure. After a predetermined period of time, this was left cooled and the zeolite membrane composite was taken out of the reaction mixture, then washed and dried at 100° C. for 4 hours or more.

The membrane composite was calcined in air in an electric furnace at 500° C. for 5 hours. The heating rate and the cooling rate were both 0.5° C./min. The mass of the CHA-type zeolite crystallized on the support, that had been obtained from the difference between the mass of the composite membrane after calcined and the mass of the support, was 150 g/m². The permeation flux of air through the calcined zeolite membrane composite was 440 L/(m²·hr).

XRD of the formed membrane confirmed the formation of CHA-type zeolite therein. In the XRD pattern, (peak intensity at around 2θ=9.6°)/(peak intensity at around 2θ=20.8°)= 3.5, and (peak intensity at around 2θ=17.9°)/(peak intensity at around 2θ=20.8°)=0.46. The peak intensity at around 2θ=9.6° is large as compared with that in XRD of the powdery CHA-type zeolite used as the seed crystal, from which the orientation to the plane (1,0,0) in rhombohedral setting is assumed.

SEM data of the zeolite membrane composite confirmed the crystals densely formed on the surface of the composite. The membrane thickness, as obtained through SEM, was about 10 µm on average. The molar ratio of $SiO_2/Al_2O_3$ in the zeolite membrane, as obtained through SEM-EDX, was 37.2.

The obtained inorganic porous support-CHA-type zeolite membrane composite was processed for the silylation treatment 1.

In the same manner as in Comparative Example 6, a part of the inorganic porous support-CHA-type zeolite membrane composite that had been processed for the silylation treatment 1 was analyzed to provide the water vapor adsorption isotherm thereof. The water adsorption per gram of the CHA-type zeolite membrane composite at a relative pressure of 0.8, as obtained from the water vapor adsorption isotherm, was 0.01072 g.

In the same manner as in Comparative Example 6, a part of the inorganic porous support-CHA-type zeolite membrane composite that had been processed for the silylation treatment 1 was immersed in an aqueous 90 mass % acetic acid solution at room temperature for 1 week. The zeolite membrane composite was taken out of the liquid, and well washed with desalted water, and then in the same manner as above, analyzed to provide the water vapor adsorption isotherm thereof. The water adsorption per gram of the CHA-type zeolite membrane composite at a relative pressure of 0.8, as obtained from the water vapor adsorption isotherm, was 0.00958 g. After immersed in the aqueous 90 mass % acetic acid solution for 1 week, the water adsorption of the CHA-type zeolite membrane composite at a relative pressure of 0.8 was 89% of the water adsorption thereof before immersion.

The inorganic porous support-CHA-type zeolite membrane composite that had been processed for the silylation treatment 1 was used for selective permeation and separation of water from a mixed solution of water/acetic acid (10/90 mass %) through vapor permeation. The inorganic porous support-CHA-type zeolite membrane composite was set in a thermostatic oven at 135° C., and the mixed solution of water/acetic acid was fed into a vaporizer at a flow rate of 0.8 cm³/min, wholly vaporized therein and applied to the inorganic porous support-CHA-type zeolite membrane composite.

After 2 hours, the permeation result was as follows. The permeation flux was 1.7 kg/(m²·hr); the separation factor was 600, and the water concentration in the permeated liquid was 99.08% by mass. The water permeance is $6.9 \times 10^{-7}$ mol/(m$^2$·sec·Pa).

Comparative Example 7

An inorganic porous support-CHA-type zeolite membrane composite was produced under the same condition as in Comparative Example 3. The zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 32.4 The difference between the molar ratio of $SiO_2/Al_2O_3$ in the zeolite membrane itself and the molar ratio of $SiO_2/Al_2O_3$ in the membrane surface was not more than 20.

The obtained inorganic porous support-CHA-type zeolite membrane composite was used for selective permeation and separation of water from a mixed solution of water/isopropanol (IPA) (10/90 mass %) through vapor permeation. The inorganic porous support-CHA-type zeolite membrane composite was set in a thermostatic oven at 120° C., and a mixed solution of water/IPA was fed into a vaporizer at a flow rate of 1.2 cm$^3$/min, wholly vaporized therein and applied to the inorganic porous support-CHA-type zeolite membrane composite.

After 4 hours, the permeation result was as follows. The permeation flux was 2.5 kg/(m$^2$·hr); the separation factor was 800, and the water concentration in the permeated liquid was 98.85% by mass. The water permeance is $1.4 \times 10^{-6}$ mol/(m$^2$·sec·Pa).

Example 12

An inorganic porous support-CHA-type zeolite membrane composite was produced under the same condition as in Comparative Example 3. The zeolite membrane composite was processed for the silylation treatment 1.

The zeolite membrane composite processed for the silylation treatment 1 was analyzed through SEM-EDX, in which the molar ratio of $SiO_2/Al_2O_3$ in the zeolite membrane itself was 20, and was analyzed through XPS, in which the molar ratio of $SiO_2/Al_2O_3$ in the zeolite membrane surface was 64.6. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 7, the inorganic porous support-CHA-type zeolite membrane composite processed for the silylation treatment 1 was used for selective permeation and separation of water from a mixed solution of water/isopropanol (IPA) (10/90 mass %) through vapor permeation.

After 4 hours, the permeation result was as follows. The permeation flux was 2.0 kg/(m$^2$·hr); the separation factor was 55000, and the water concentration in the permeated liquid was 99.98% by mass. The water permeance is $1.1 \times 10^{-6}$ mol/(m$^2$·sec·Pa).

From the results in Comparative Example 7 and Example 12, it is known that the separation factor increased by 69 times by increasing the molar ratio of $SiO_2/Al_2O_3$ in the zeolite membrane surface to be larger by at least 20 than the molar ratio of $SiO_2/Al_2O_3$ in the zeolite membrane itself.

Example 13

An inorganic porous support-CHA-type zeolite membrane composite was produced under the same condition as in Comparative Example 3. The zeolite membrane composite was put in a Teflon®-made inner cylinder, as immersed in 121.5 g of desalted water, 2.5 g of tetraethoxysilane (TEOS) and 13.5 g of aqueous 1 mol/l nitric acid solution in the vertical direction therein, then the autoclave was sealed up, and heated at 100° C. for 20 hours under autogenous pressure. After a predetermined period of time, this was left cooled and the zeolite membrane composite was taken out and washed with desalted water. Hereinafter this treatment is referred to as "silylation treatment 7". The pH of the processing solution used for the silylation treatment 7 was 1.3, the H$^+$ concentration thereof was 0.05 mol/l, and the Si content thereof was 0.24% by mass.

After processed for the silylation treatment 7, the zeolite membrane composite was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 95.0 The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 7, the inorganic porous support-CHA-type zeolite membrane composite that had been processed for the silylation treatment 7 was used for selective permeation and separation of water from a mixed solution of water/isopropanol (IPA) (10/90 mass %) through vapor permeation.

After 4 hours, the permeation result was as follows. The permeation flux was 1.7 kg/(m$^2$·hr); the separation factor was 74500, and the water concentration in the permeated liquid was 99.99% by mass. The water permeance is $9.9 \times 10^{-7}$ mol/(m$^2$·sec·Pa).

From the results in Comparative Example 7 and Example 13, it is known that the separation factor increased by 93 times by increasing the molar ratio of $SiO_2/Al_2O_3$ in the zeolite membrane surface to be larger by at least 20 than the molar ratio of $SiO_2/Al_2O_3$ in the zeolite membrane itself.

Example 14

An inorganic porous support-CHA-type zeolite membrane composite was produced under the same condition as in Comparative Example 3. The top and the bottom of the zeolite membrane composite were sealed up each with a silicon rubber plug, and then immersed in Mitsubishi Chemical's MKC® Silicate, MS51 (methyl silicate oligomer with $SiO_2$ content of 52.0±1.0%) for silylation treatment in such a manner that the zeolite membrane composite could be wholly immersed therein, and after kept as such for 5 seconds, the zeolite membrane composite was pulled up, then left as such for 1 hour, and dried in an oven with water existing therein, at 100° C. for 4 hours. The treatment is referred to as "silylation treatment 8".

The zeolite membrane composite processed for the silylation treatment 8 was analyzed through SEM-EDX, in which the molar ratio of $SiO_2/Al_2O_3$ in the zeolite membrane itself was 17, and was analyzed through XPS, in which the molar ratio of $SiO_2/Al_2O_3$ in the zeolite membrane surface was 626.4. The molar ratio of $SiO_2/Al_2O_3$ in the zeolite membrane surface is larger by at least 20 than the molar ratio of $SiO_2/Al_2O_3$ in the zeolite membrane itself, and it may be presumed that the zeolite membrane surface could be modified with an Si compound.

In the same manner as in Comparative Example 7, the inorganic porous support-CHA-type zeolite membrane composite that had been processed for the silylation treatment 8 was used for selective permeation and separation of water from a mixed solution of water/isopropanol (IPA) (10/90 mass %) through vapor permeation.

After 4 hours, the permeation result was as follows. The permeation flux was 1.9 kg/(m²·hr); the separation factor was 198800, and the water concentration in the permeated liquid was 99.99% by mass. The water permeance is $1.2 \times 10^{-6}$ mol/(m²·sec·Pa).

From the results in Comparative Example 7 and Example 14, it is known that the separation factor increased by 249 times by increasing the molar ratio of $SiO_2/Al_2O_3$ in the zeolite membrane surface to be larger by at least 20 than the molar ratio of $SiO_2/Al_2O_3$ in the zeolite membrane itself.

The results in Comparative Examples 1 to 5, and Examples 1 to 9 and 12 to 14 are shown in Table 1, and the results in Comparative Example 6, and Examples 10 and 11 are in Table 2.

TABLE 1

| | Support | Method of Silylation Treatment | | Molar Ratio of $SiO_2/Al_2O_3$ | | Separation Condition |
| | | Processing Solution | Treatment Condition | SEM-EDX | XPS | Substance to be separated |
| --- | --- | --- | --- | --- | --- | --- |
| Comparative Example 1 | mullite | — | — | 17 | 36.2 | water/acetic acid = 5/95 |
| Example 1 | mullite | TEOS/sulfuric acid aqueous solution | 100° C. 20 hrs | 19 | 109.8 | water/acetic acid = 5/95 |
| Example 2 | mullite | TEOS/acetic acid aqueous solution | 100° C. 20 hrs | 15 | 91.2 | water/acetic acid = 5/95 |
| Comparative Example 2 | mullite | — | — | 17 | 36.2 | water/acetic acid = 10/90 |
| Example 3 | mullite | TEOS/phosphoric acid aqueous solution | 100° C. 20 hrs | 17 | 90.0 | water/acetic acid = 10/90 |
| Example 4 | mullite | colloidal silica aqueous solution | 100° C. 21 hrs | 17 | 43.6 | water/acetic acid = 10/90 |
| Comparative Example 3 | alumina | — | — | 17 | 32.4 | water/phenol = 10/90 |
| Example 5 | alumina | TEOS/acetic acid aqueous solution | 100° C. 20 hrs | 17 | 60.4 | water/phenol = 10/90 |
| Comparative Example 4 | mullite | — | — | 17 | 36.2 | water/acetic acid = 10/90 |
| Example 6 | mullite | TEOS/sulfuric acid aqueous solution | 100° C. 20 hrs | 19 | 109.8 | water/acetic acid = 10/90 |
| Comparative Example 5 | alumina | — | — | 17 | 32.4 | water/acetic acid = 10/90 |
| Example 7 | alumina | TEOS/APTS toluene solution | 100° C. 8 hrs | 17 | 146.4 | water/acetic acid = 10/90 |
| Example 8 | mullite | TEOS/lacetic acid aqueous solution | 100° C. 20 hrs | 22 | 44.2 | — |
| Example 9 | mullite | TEOS/acetic acid aqueous solution | 100° C. 20 hrs | 28 | 57.6 | — |
| Comparative Example 7 | alumina | — | — | 17 | 32.4 | water/IPA = 10/90 |
| Example 12 | alumina | TEOS/sulfuric acid aqueous solution | 100° C. 20 hrs | 20 | 64.6 | water/IPA = 10/90 |
| Example 13 | alumina | TEOS/sulfuric acid aqueous solution | 100° C. 20 hrs | 17 | 95.0 | water/IPA = 10/90 |
| Example 14 | alumina | MSS1 | Immersion at room temperature for 5 sec, drying at 100° C. for 4 hrs | 17 | 626.4 | water/IPA = 10/90 |

| | Separation Condition | Permeation | | |
| | Temperature | Flux kg/(m²/hr) | Separation Factor | Permeance $10^{-6}$ mol/(m² · sec · Pa) |
| --- | --- | --- | --- | --- |
| Comparative Example 1 | 90° C. | 1.3 | 400 | 1.5 |
| Example 1 | 90° C. | 0.92 | 17,900 | 1.2 |
| Example 2 | 90° C. | 1.2 | 210,000 | 1.7 |
| Comparative Example 2 | 90° C. | 1.8 | 1,900 | 1.3 |
| Example 3 | 90° C. | 1.7 | 99,100 | 1.3 |
| Example 4 | 90° C. | 2.3 | 91,000 | 1.6 |
| Comparative Example 3 | 75° C. | 5.8 | 700 | 2.9 |
| Example 5 | 75° C. | 5.2 | 75,500 | 2.7 |
| Comparative Example 4 | 130° C. | 2.8 | 5 | 0.55 |
| Example 6 | 130° C. | 0.88 | 18,000 | 0.50 |
| Comparative Example 5 | 130° C. | 1.4 | 40 | 0.63 |
| Example 7 | 130° C. | 0.84 | 500 | 0.45 |
| Example 8 | — | — | — | — |
| Example 9 | — | — | — | — |

TABLE 1-continued

|   | | | | |
|---|---|---|---|---|
| Comparative Example 7 | 120° C. | 2.5 | 800 | 1.4 |
| Example 12 | 120° C. | 2.0 | 55,000 | 1.1 |
| Example 13 | 120° C. | 1.7 | 74,500 | 0.99 |
| Example 14 | 120° C. | 1.9 | 198,800 | 1.2 |

TABLE 2

| | Support | Method of Silylation Treatment | | Water Adsorption (g/g) | | Separation Condition | | Permeation Flux kg/(m²/hr) | Separation Factor | Permeance 10⁻⁶ mol/ (m² · sec · Pa) |
|---|---|---|---|---|---|---|---|---|---|---|
| | | Processing Solution | Treatment Condition | before immersion | after immersion | Substance to be separated | Temperature | | | |
| Comparative Example 6 | mullite | — | — | 0.01423 | 0.01135 | water/acetic acid = 10/90 | 90° C. | 1.8 | 1,900 | 1.3 |
| Example 10 | mullite | TEOS/acetic acid aqueous solution | 100° C. 20 hrs | 0.01368 | 0.01275 | water/acetic acid = 10/90 | 90° C. | 1.7 | 96,400 | 1.2 |
| Example 11 | alumina | TEOS/sulfuric acid aqueous solution | 100° C. 20 hrs | 0.01072 | 0.00958 | water/acetic acid = 10/90 | 135° C. | 1.7 | 600 | 0.69 |

While the present invention has been described in detail and with reference to specific embodiments thereof, it will be apparent to one skilled in the art that various changes and modifications can be made therein without departing from the spirit and scope thereof. The present application is based upon a Japanese patent application filed Feb. 24, 2012 (Patent Application 2012-039271) and a Japanese patent application filed Aug. 28, 2012 (Patent Application 2012-187576), the contents of which are incorporated herein by reference.

INDUSTRIAL APPLICABILITY

The invention is usable in any industrial field and is especially preferred for use in the field that requires separation of water from water-containing organic compounds and recovery of organic compounds, for example, in chemical plants, fermentation plants, factories for precision electronic components, cell production factories, etc.

REFERENCE SIGNS LIST

1 Stirrer
2 Hot-Water Bath
3 Stirring Blade
4 Liquid to be Separated
5 Zeolite Membrane Composite
6 Pirani Gauge
7 Permeated Liquid Collecting Trap
8 Cold Trap
9 Vacuum Pump
10 Liquid to be Separated
11 Feeding Pump
12 Vaporizer
13 Thermostatic Oven
14 Zeolite Membrane Composite Module
15 Collecting Trap of Liquid to be Separated
16 Permeated Liquid Collecting Trap
17 Cold Trap
18 Vacuum Pump

The invention claimed is:

1. A porous support-zeolite membrane composite comprising:
a tubular inorganic porous support selected from the group consisting of alumina and mullite, and
a zeolite membrane provided on the tubular inorganic porous support,
wherein:
the zeolite membrane comprises a zeolite having a microporous structure of oxygen-containing rings, wherein each oxygen-containing ring comprises 8 or fewer oxygen atoms,
a molar ratio of $SiO_2/Al_2O_3$ in a surface of the zeolite membrane is larger by at least 25 than a molar ratio of $SiO_2/Al_2O_3$ in the zeolite membrane itself,
the molar ratio of $SiO_2/Al_2O_3$ in the zeolite membrane itself is a value obtained through scanning electron microscope-energy dispersive X-ray spectroscopy (SEM-EDX), wherein the sample is analyzed at an X-ray accelerating voltage of 10 kV, and
the molar ratio of $SiO_2/Al_2O_3$ in the surface of the zeolite membrane is a value obtained through X-ray photoelectron spectroscopy (XPS) using Al-Kα with takeoff angle of 45°.

2. The porous support-zeolite membrane composite according to claim 1, wherein a water adsorption of the porous support-zeolite membrane composite at a relative pressure of 0.8, as determined from a water vapor adsorption isotherm of the porous support-zeolite membrane composite, is at least 82% of a water adsorption of the porous support-zeolite membrane composite under the same condition as above after a one-week immersion of the porous support-zeolite membrane composite in an aqueous 90 mass % acetic acid solution at room temperature.

3. The porous support-zeolite membrane composite according to claim 1, wherein a molar ratio of $SiO_2/Al_2O_3$ in a surface of the zeolite membrane is larger by at least 30 than a molar ratio of $SiO_2/Al_2O_3$ in the zeolite membrane itself.

4. The porous support-zeolite membrane composite according to claim 1, wherein the molar ratio of $SiO_2/Al_2O_3$ in the surface of the zeolite membrane is from 25 to 3000.

5. The porous support-zeolite membrane composite according to claim 1, wherein the molar ratio of $SiO_2/Al_2O_3$ in the zeolite membrane itself is from 5 to 2000.

6. The porous support-zeolite membrane composite according to claim 1, wherein the zeolite having a microporous structure of oxygen-containing rings is a CHA-type zeolite.

7. The porous support-zeolite membrane composite according to claim 1, wherein in a X-ray diffraction pattern obtained through irradiation to the zeolite membrane surface with X-ray, a peak intensity at around $2\theta=17.9°$ is at least 0.5 times a peak intensity at around $2\theta=20.8°$.

8. The porous support-zeolite membrane composite according to claim 1, wherein in a X-ray diffraction pattern obtained through irradiation to the zeolite membrane surface with X-ray, a peak intensity at around $2\theta=9.6°$ is at least 2 times a peak intensity at around $2\theta=20.8°$.

9. A method of producing a porous support-zeolite membrane composite according to claim 1, comprising forming the zeolite membrane on the tubular inorganic porous support through hydrothermal synthesis using an aqueous reaction mixture that contains an Si element source, an Al element source and an alkali source.

10. The method according to claim 9, wherein the alkali source comprises potassium.

11. The method according to claim 9, further comprising immersion-treating the zeolite membrane in a solution containing one or more Si element sources selected from the group consisting of tetraethoxysilane, tetramethoxysilane, methyltriethoxysilane, 3-aminopropyltriethoxysilane, amorphous silica, fumed silica, colloidal silica, silica gel, sodium silicate, silicate oligomer, and silica sol.

12. A separation or concentration method, which comprises bringing a gas or liquid mixture of multiple components into contact with the porous support-zeolite membrane composite of claim 1 to thereby make a highly-permeative substance in the mixture pass through the membrane composite so as to separate the highly-permeative substance from the mixture, or to thereby make the highly-permeative substance separated from the mixture so as to concentrate a poorly-permeative substance in the mixture.

13. The method according to claim 12, wherein the gas or liquid mixture of multiple components is a mixture of an organic compound and water.

14. The method according to claim 13, wherein the organic compound is at least one compound selected from the group consisting of an organic acid, an alcohol, an ether, an aldehyde, a ketone, an ester and a nitrogen-containing organic compound.

15. The porous support-zeolite membrane composite according to claim 1, wherein the surface of the zeolite membrane comprises Si—OH groups.

16. The porous support-zeolite membrane composite according to claim 1, wherein fine defects existing in the surface of the zeolite membrane are blocked.

* * * * *